(12) United States Patent
Peneva et al.

(10) Patent No.: US 9,131,708 B2
(45) Date of Patent: Sep. 15, 2015

(54) PROBIOTICS FOR DIETARY DAIRY PRODUCT

(75) Inventors: Daniela Peneva, Sofia (BG); Nikola Aleksandrov, Sofia (BG)

(73) Assignee: Daflorn LTD, Sofia (BG)

( * ) Notice: Subject to any disclaimer, the term of this patent is extended or adjusted under 35 U.S.C. 154(b) by 212 days.

(21) Appl. No.: 13/557,597

(22) Filed: Jul. 25, 2012

(65) Prior Publication Data
US 2013/0236600 A1    Sep. 12, 2013

(30) Foreign Application Priority Data

Mar. 7, 2012    (BG) ........................................ 111161

(51) Int. Cl.
| | |
|---|---|
| *A23C 9/127* | (2006.01) |
| *C12R 1/46* | (2006.01) |
| *C12R 1/225* | (2006.01) |
| *A23L 1/30* | (2006.01) |
| *C12N 1/20* | (2006.01) |

(52) U.S. Cl.
CPC ............... *A23C 9/127* (2013.01); *A23L 1/3014* (2013.01); *C12N 1/20* (2013.01); *C12R 1/225* (2013.01); *C12R 1/46* (2013.01); *A23Y 2220/29* (2013.01); *A23Y 2220/39* (2013.01); *A23Y 2240/75* (2013.01)

(58) Field of Classification Search
None
See application file for complete search history.

(56) References Cited

FOREIGN PATENT DOCUMENTS

BG    52041    12/1996

OTHER PUBLICATIONS

Courtin et al., Interaction between microorganisms in a simple ecosystem: yogurt bacteria as a study model, Lait (84), 125-134, 2004.*
Begovic et al., Analysis of Dominant Lactic Acid Bacteria From Artisanal Raw Milk Cheeses Produced on the Mountain Stara Planina, Serbia., Arch. Biol. Sci., Belgrade, 63 (1), 11-20, 2011.*

* cited by examiner

*Primary Examiner* — Taeyoon Kim
*Assistant Examiner* — Srikanth Patury
(74) *Attorney, Agent, or Firm* — Andrea M. Porterfield; Polsinelli PC

(57) ABSTRACT

The present invention relates to compositions containing probiotic microorganisms and methods of making and using probiotic associations containing these microorganisms. More particularly, the invention relates to an association of probiotic lactic acid microorganisms including newly identified strains of microorganisms and their use in dietary products. These microorganisms are cultured to produce a protective shell that enhances shelf-stability of compositions and products of the invention. The isolated microorganisms include new strains of *Lactobacillus delbrueckii* subsp. *bulgaricus*, *Lactobacillus helveticus*, *Lactobacillus delbrueckii* subsp. *lactis*, and *Streptococcus thermophillus*.

11 Claims, 16 Drawing Sheets

US 9,131,708 B2

PROBIOTICS FOR DIETARY DAIRY PRODUCT

CROSS-REFERENCE TO RELATED APPLICATION

This application claims benefit of Bulgaria Application No. 111 161/07.03.2012, filed Mar. 7, 2012 with the Patent Office of the Republic of Bulgaria and is hereby incorporated by reference.

FIELD OF THE INVENTION

The present invention relates to compositions containing probiotic microorganisms and methods of making and using such microorganisms. More particularly, the invention relates to an association of probiotic lactic acid microorganisms including newly identified strains of microorganisms and their use in dietary products.

BACKGROUND OF THE INVENTION

Products obtained by lactic acid fermentation are known to have been produced for centuries. These dietary products are consumed daily by the majority of people starting at a very early age. In order to produce these dietary products, various strains of lactic acid microorganisms having probiotic properties are used independently or in combination.

*Lactobacillus delbrueckii* subsp. *bulgaricus* is a specific type of microorganism known to be of plant origin and differs significantly from other probiotic bacteria. Under natural conditions, this bacterium grows only in a certain geographical territory overlapping the territory of Bulgaria and to a great extent corresponding to the territory of Ancient Thrace. Beyond this geographic territory, the microorganism mutates and its growth is stunted. Also, *Lactobacillus delbrueckii* subsp. *bulgaricus* is known to only cooperate with *Streptococcus thermophilus* during lactic acid fermentation and in the human and animal body. In this unique cooperation these two microorganisms work symbiotically to synergistically produce multiple positive effects and balanced side effects. These beneficial effects include a positive effect on the natural micro-flora of people, competitive exclusion of pathogens and stimulation/modulation of mucosal immunity.

Based on the knowledge that *Lactobacillus delbrueckii* subsp. *bulgaricus* can cooperate with *Streptococcus thermophilus* during lactic acid fermentation, as well as in the human and animal body, traditionally only dairy products or isolates of human and/or animal and/or plant origin are used as the main source of finding new strains of probiotic lactic acid microorganisms. This focused searching excludes the identification of such organisms from other sources that may have enhanced and desired characteristics such as superior probiotic properties and enhanced shelf life. Accordingly, a need still exists for newly identified microorganisms capable of productive lactic acid fermentation in the presence of additional microorganisms and having superior probiotic properties with enhanced shelf stability.

SUMMARY OF THE INVENTION

The present invention is directed to newly identified microorganisms isolated from a natural water spring in Mountains Stara Planina, Central Region of Northern Bulgaria. These isolated microorganisms include a strain of *Lactobacillus delbrueckii* subsp. *bulgaricus* that does not exhibit stunted growth compared to known *Lactobacillus delbrueckii* subsp. *bulgaricus* isolates. The isolated microorganisms are capable of productive lactic acid fermentation in the presence of each other and provide a probiotic association useful in dietary products. Also, the isolated microorganisms have a protective shell that enhances their viability after exposure to extreme conditions and lengthy storage conditions. The present invention is directed to compositions and methods related to the isolated microorganisms.

In one aspect, the invention includes an isolated microorganism starting material including milk and at least two microorganisms. Suitable microorganisms include *Lactobacillus delbrueckii* subsp. *bularicus, Lactobacillus helveticus, Lactobacillus delbrueckii* subsp. *lactis, Streptococcus thermophillus*, and combinations thereof. In one embodiment the microorganisms include at least one strain of *Lactobacillus delbrueckii* subsp. *bulgaricus* DWT1 deposited with the Czech Collection of Microorganisms (CCM) as no. 7992, *Lactobacillus helveticus* DWT2 deposited with the CCM as no. 7993, *Lactobacillus delbrueckii* subsp. *lactis* DWT3 deposited with the CCM as no. 7994, *Streptococcus thermophillus* DWT4 deposited with the CCM as no. 7992, *Streptococcus thermophillus* DWT5 deposited with the CCM as no. 7993, *Streptococcus thermophillus* DWT6 deposited with the CCM as no. 7994, *Streptococcus thermophillus* DWT7 deposited with the CCM as no. 7995, *Streptococcus thermophillus* DWT8 deposited with the CCM as no. 7996, and combinations thereof.

In one aspect, the invention includes the co-culture of two or more microorganisms resulting in a probiotic association that is beneficial when administered to a subject. The probiotic association is maintained during the methods of the invention resulting in a dietary product with probiotic properties.

The dietary products of the invention include a starting material consisting of at least two microorganism selected from the group consisting of *Lactobacillus delbrueckii* subsp. *bularicus, Lactobacillus helveticus, Lactobacillus delbrueckii* subsp. *lactis, Streptococcus thermophillus*, and combinations thereof. Suitable strains of these microorganisms include *Lactobacillus delbrueckii* subsp. *bulgaricus* DWT1 deposited with the Czech Collection of Microorganisms (CCM) as no. 7992, *Lactobacillus helveticus* DWT2 deposited with the CCM as no. 7993, *Lactobacillus delbrueckii* subsp. *lactis* DWT3 deposited with the CCM as no. 7994, *Streptococcus thermophillus* DWT4 deposited with the CCM as no. 7992, *Streptococcus thermophillus* DWT5 deposited with the CCM as no. 7993, *Streptococcus thermophillus* DWT6 deposited with the CCM as no. 7994, *Streptococcus thermophillus* DWT7 deposited with the CCM as no. 7995, *Streptococcus thermophillus* DWT8 deposited with the CCM as no. 7996, and combinations thereof.

In some aspects, the dietary products of the invention include from about $8.0 \times 10^7$ cfu/g to $1.2 \times 10^8$ cfu/g of microorganisms. In certain aspects, the dietary products include from about $4.6 \times 10^7$ cfu/g to $5.9 \times 10^7$ cfu/g of *Streptococcus thermophilus* microorganisms. Suitable *Streptococcus thermophilus* microorganisms include *Streptococcus thermophillus* DWT4, CCM reg. No. 7992, *Streptococcus thermophillus* DWT5, CCM reg. No. 7993, *Streptococcus thermophillus* DWT6, CCM reg. No. 7994, *Streptococcus thermophillus* DWT7, CCM reg. No 7995, *Streptococcus thermophillus* DWT8, CCM reg. No. 7996, and combinations thereof. In some aspects, the dietary products include from about $6.1 \times 10^6$ cfu/g to $7.8 \times 10^6$ cfu/g of the strain *Lactobacillus delbrueckii* ssp. *lactis* DWT3, CCM reg. No. 7994. In some aspects, the dietary products include from about $1.4 \times 10^7$ cfu/g to $2.9 \times 10^7$ cfu/g of the strain *Lactobacillus delbrueckii* ssp. *bulgaricus* DWT1, CCM reg. No. 7992. In some aspects, the dietary products include from about from $1.4 \times 10^7$ to $2.8 \times 10^7$ cfu/g of the strain *Lactobacillus helveticus* DWT2, CCM reg. No. 7993.

In another aspect, the invention includes methods of using microorganisms to produce dietary products. In one embodiment, the methods include a method of producing a starter material. In another embodiment, the methods include a method of producing a dietary product from the starter material.

In one aspect, methods of the invention include culturing microorganism strains of *Lactobacillus delbrueckii* subsp. *bulgaricus, Lactobacillus helveticus, Lactobacillus delbrueckii* subsp. *lactis, Streptococcus thermophillus,* and combinations thereof to produce a probiotic association, fermenting the probiotic association to produce a fermentation product, adding milk to the fermentation product, neutralizing the fermentation product to an optimal pH, and lyophilizing the fermentation product to produce a starter material.

In another aspect, methods of the invention mixing starter material with an aqueous solution of milk and sugar to produce an aqueous starter material mixture, fermenting the starter material mixture to produce a fermentation product, and lyophilizing the fermentation product to produce a dietary product.

In one embodiment, the dietary product is combined with a nutritional supplement. Any suitable nutritional supplement known in the art that is compatiable with the dietary product of the invention is contemplated. Exemplary nutritional supplements include, without limitation, oils, plant extracts, fibers, enzymes, honey, blueberry extract, papaya extract, cocoa, coffee, and combinations thereof.

The compositions and products of the present invention are shelf-stable for several months including at least 1, 2, 3, 4, 5, 6, 7, 8, 9, 10, 11, 12, 13, 14, 15, 16, 17, 18, 19, 20, 21, 22, 23 or more months.

BRIEF DESCRIPTION OF DEPOSITS OF BIOLOGICAL MATERIAL

The microorganisms described herein were deposited on Feb. 20, 2012, in the Czech Collection of Microorganisms (CCM) at Masaryk University 602 00 BRNO, Tvrdého 14, CZECH REPUBLIC under the terms and conditions of the Budapest Treaty on the International Recognition of the Deposit of Microorganisms for the Purposes of Patent Procedure. Each microorganism was registered under a CCM accession number as provided below:

Strain *Lactobacillus delbrueckii* subsp. *bulgaricus* DWT1, CCM reg. No. 7992;

Strain *Lactobacillus helveticus* DWT2, CCM reg. No. 7993;

Strain *Lactobacillus delbrueckii* subsp. *lactis* DWT3, CCM reg. No. 7994;

Strain *Streptococcus thermophillus* DWT4, CCM reg. No. 7992;

Strain *Streptococcus thermophillus* DWT5, CCM reg. No. 7993;

Strain *Streptococcus thermophillus* DWT6, CCM reg. No. 7994;

Strain *Streptococcus thermophillus* DWT7, CCM reg. No. 7995; and,

Strain *Streptococcus thermophillus* DWT8, CCM reg. No. 7996.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows the macrorestriction profile, obtained after restriction with SmaI enzyme of genomic DNA of isolates *Streptococcus thermophilus* from sample IN 1. (Key: Lane 1—isolate *Streptococcus thermophilus* i22, Lane 2—isolate *Streptococcus thermophilus* i21, Lane 3—isolate *Streptococcus thermophilus* i24, Lane 4—isolate *Streptococcus thermophilus* i26, Lane 5—isolate *Streptococcus thermophilus* i31, Lane 6—isolate *Streptococcus thermophilus* i32, Lane 7—isolate *Streptococcus thermophilus* i34, m—pulsed—field marker 0.1-200 kbp);

FIG. 2 shows the macrorestriction profile, obtained after restriction with XhoI enzyme of genomic DNA of isolate *Lactobacillus* from sample IN1. (Key: Lane 1—isolate *Lactobacillus helveticus* i1m, Lane 2—isolate *Lactobacillus helveticus* i5m, Lane 3—isolate *L. delbrueckii* ssp. *bulgaricus* i2m, Lane 4—isolate *L. delbrueckii* ssp. *bulgaricus* i4s, Lane 5—isolate *L. delbrueckii* ssp. *lactis* i3L, Lane 6—isolate *L. delbrueckii* ssp. *lactis* i7L, m—pulsed—field marker 0.1-200 kbp);

FIG. 3 shows the macrorestriction profile, obtained after restriction with SmaI enzyme of genomic DNA of isolate *Streptococcus thermophilus* i22 from sample IN1 with indicated size of the obtained restriction fragments. (Key: Lane 1—isolate *Streptococcus thermophilus* i22, m—pulsed-field marker 0.1-200 kbp);

FIG. 4 shows the macrorestriction profile, obtained after restriction with SmaI enzyme of genomic DNA of isolate *Streptococcus thermophilus* i21 from sample IN1 with indicated size of the obtained restriction fragments. (Key: Lane 1—isolate *Streptococcus thermophilus* i22, Lane 2—isolate *Streptococcus thermophilus* i21, m—pulsed-field marker 0.1-200 kbp);

FIG. 5 shows the macrorestriction profile, obtained after restriction with SmaI enzyme of genomic DNA of isolate *Streptococcus thermophilus* i26 from sample IN1 with indicated size of the obtained restriction fragments. (Key: Lane 1—isolate *Streptococcus thermophilus* i22, Lane 2—isolate *Streptococcus thermophilus* i21, Lane 3—isolate *Streptococcus thermophilus* i24, Lane 4—isolate *Streptococcus thermophilus* i26, m—pulsed-field marker 0.1-200 kbp);

FIG. 6 shows the macrorestriction profile, obtained after restriction with SmaI enzyme of genomic DNA of isolate *Streptococcus thermophilus* i31 from sample IN1 with indicated size of the obtained restriction fragments. (Key: Lane 1—isolate *Streptococcus thermophilus* i22, Lane 2—isolate *Streptococcus thermophilus* i21, Lane 3—isolate Streptococcus thermophilus i24, Lane 4—isolate *Streptococcus thermophilus* i26, Lane 5—isolate *Streptococcus thermophilus* i31, m—pulsed-field marker 0.1-200 kbp);

FIG. 7 shows the macrorestriction profile, obtained after restriction with SmaI enzyme of genomic DNA of isolate *Streptococcus thermophilus* i32 from sample IN1 with indicated size of the obtained restriction fragments. (Key: Lane 1—isolate *Streptococcus thermophilus* i22, Lane 2—isolate *Streptococcus thermophilus* i21, Lane 3—isolate *Streptococcus thermophilus* i24, Lane 4—isolate *Streptococcus thermophilus* i26, Lane 5—isolate *Streptococcus thermophilus* i31, Lane 6—isolate *Streptococcus thermophilus* i32, m—pulsed-field marker 0.1-200 kbp);

FIG. 8 shows the macrorestriction profile, obtained after restriction with XhoI enzyme of genomic DNA of isolate *Lactobacillus helveticus* i1m from sample IN1 with indicated size of the obtained restriction fragments. (Key: Lane 1—isolate *Lactobacillus helveticus* i1m, m—pulsed-field marker 0.1-200 kbp);

FIG. 9 shows the macrorestriction profile, obtained after restriction with XhoI enzyme of genomic DNA of isolate *Lactobacillus delbrueckii* ssp. *bulgaricus* i2m from sample IN1 with indicated size of the obtained restriction fragments. (Key: Lane 1—isolate *Lactobacillus helveticus* i1m, Lane 2—isolate *Lactobacillus helveticus* i5m, Lane 3—isolate *L. delbrueckii* ssp. *bulgaricus* i2m, m—pulsed-field marker 0.1-200 kbp);

FIG. 10 shows the macrorestriction profile, obtained after restriction with XhoI enzyme of genomic DNA of isolate *Lactobacillus delbrueckii* ssp. *lactis* i3L from sample IN1 with indicated size of the obtained restriction fragments. (Key: Lane 1—isolate *Lactobacillus helveticus* i1m, Lane 2—isolate *Lactobacillus helveticus* i5m, Lane 3—isolate *L. delbrueckii* ssp. *bulgaricus* i2m, Lane 4—isolate *L. delbrueckii* ssp. *bulgaricus* i4s, Lane 5—isolate *L. delbrueckii* ssp. *lactis* i3L, m—pulsed-field marker 0.1-200 kbp);

FIG. 11 shows the macrorestriction profile, obtained after restriction with SmaI enzyme of genomic DNA of isolates *Streptococcus thermophilus* from studied samples. (Key: Lane 5—Sample P2, isolate *Streptococcus thermophilus* Pk2/1, Lane 6—Sample P2, isolate *Streptococcus thermophilus* Pk2/2, Lane 7—Sample P1, isolate *Streptococcus thermophilus* Pk1/1, Lane 8—Sample P1, isolate *Streptococcus thermophilus* Pk1/2, Lane 9—Sample P1, isolate *Streptococcus thermophilus* Pk1/3, m—pulsed-field marker 0.1-200 kbp);

FIG. 12 shows the macrorestriction profile, obtained after restriction with XhoI enzyme of genomic DNA of isolates *Lactobacillus delbrueckii* ssp. *lactis* from studied samples. (Key: Lane 1—Sample P3, isolate *L. delbrueckii* ssp. *lactis* Pp3/1; Lane 2—Sample P3, isolate *L. delbrueckii* ssp. *lactis* Pp 3/3; Lane 3—Sample P3, isolate *L. delbrueckii* ssp. *lactis* Pp 3/5; Lane 4—Sample P3, isolate *L. delbrueckii* ssp. *lactis* Pp 3/6; Lane 5—Sample P2, isolate *L. delbrueckii* ssp. *lactis* Pp 2/2; Lane 6—Sample P2, isolate *L. delbrueckii* ssp. *lactis* Pp 2/3; Lane 7—Sample P2, isolate *L. delbrueckii* ssp. *lactis* Pp 2/4; Lane 8—Sample P2, isolate *L. delbrueckii* ssp. *lactis* Pp 2/5; M—pulsed-field marker 0.1-200 kbp);

FIG. 13 shows the macrorestriction profile, obtained after restriction with XhoI enzyme of genomic DNA of isolates *Lactobacillus delbrueckii* ssp. *lactis* from studied samples. (Key: Lane 1—Sample P3, isolate *L. delbrueckii* ssp. *lactis* Pp 3/6; Lane 2—Sample P2, isolate *L. delbrueckii* ssp. *lactis* Pp 2/3; Lane 5—Isolate *L. delbrueckii* ssp. *lactis* i3L from sample IN1 (Protocol 24.6.11r.); M—pulsed-field marker 0.1-200 kbp);

DETAILED DESCRIPTION

Figure 1:
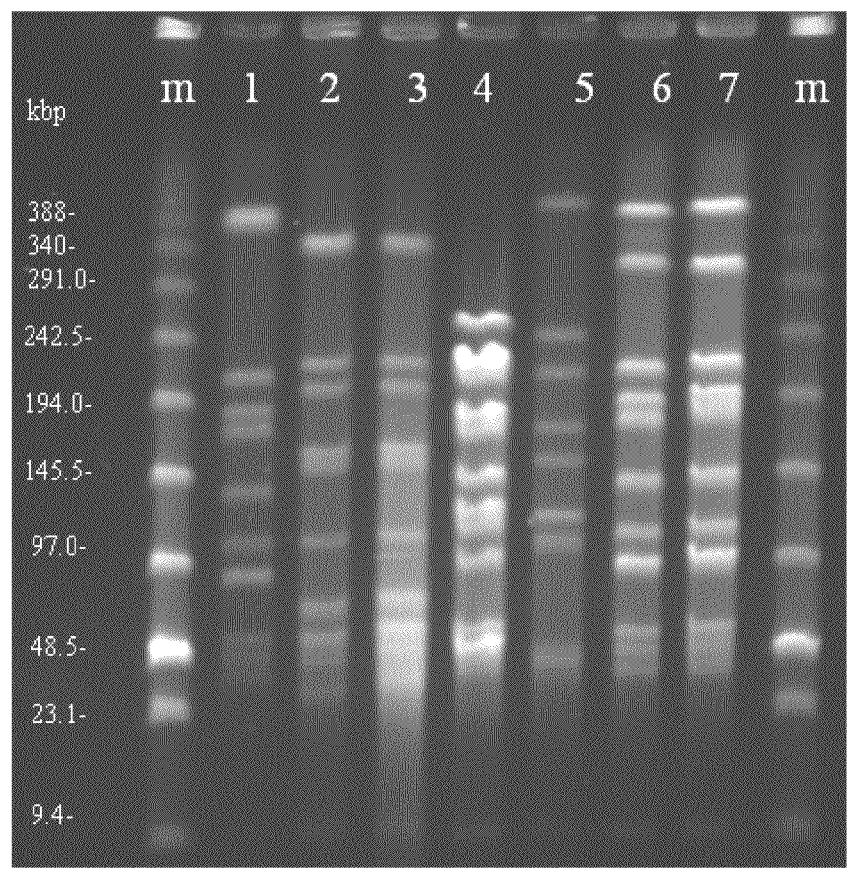
FIG. 1 shows the macrorestriction profiles of isolates of *Streptococcus thermophillus*, of the probiotic association. Specifically.

In accordance with the present invention, compositions including multiple microorganisms as well as methods of use have been discovered. In particular, it has been discovered that a consortium of microorganisms having a probiotic association can be cultured to produce compositions having enhanced stability and shelf-life. Such compositions are useful in dietary products.

I. Compositions

Compositions useful in this invention include microorganisms and additives. The microorganisms may include species of *Lactobacillus* and *Streptococcus*.

Suitable microorganisms include those commonly known in the art as lactic acid or probiotic microorganisms. Exemplary microorganisms include *Lactobacillus delbrueckii* subsp. *bulgaricus*, *Lactobacillus delbrueckii* subsp. *lactis*, *Lactobacillus helveticus*, *Streptococcus thermophilus*, and combinations thereof.

Preferably, at least one microorganism is included in the compositions of the invention. More preferably, the compositions include consortiums of two or more microorganisms. It is contemplated that where two or more microorganisms form the composition, the microorganisms are co-cultured. The microorganisms may be propagated by methods known in the art. For example, the microorganisms may be propagated in a liquid medium under anaerobic or aerobic conditions. Suitable liquid mediums used for growing microorganism include those known in the art.

In one aspect, the composition includes a total number of microorganisms of about 1 to about 1 billion colony forming units (CFU) per gram (g). Preferably, the composition includes a total number of microorganisms of about 100,000 to about 800 million CFU per gram. More preferably, the composition includes a total number of microorganisms of about 1 million to about 500 million CFU per gram. Most preferably, the composition includes a total number of microorganisms of about 80 million to about 120 million CFU per gram.

In one aspect, the composition includes living and non-living microorganisms. In another aspect, the composition includes living or non-living microorganisms. Compositions may contain extracts of the microorganisms. Such extracts may be considered a liquid fermentation product of the living microorganisms. The extracts of microorganisms include, by way of example, enzymes, metabolites, proteins, and other substances that are produced by microorganisms and are capable of eliciting an effect on an environment regardless of the living status of the microorganism.

In one aspect, the composition is fermented to produce a fermentation product. The composition may be fermented for about 1, 2, 3, 4, 5, 6, 7, 8, 9, 10, 11, 12 or more hours or for about 1, 2, 3, 4, 5, 6, 7, 8, 9, 10, 11, 12, 13, 14, 15, 16, 17, 18, 19, 20, 21, 22, 23, 24, 25, or more days. Preferably, the composition is fermented for at least about 5 hours. More preferably, the composition is fermented for at least 3 hours.

The compositions may also include additives. Suitable additives include substances known in the art that may support growth, production of specific metabolites by the microorganism, alter pH, enrich for target metabolites, enhance insecticidal effects, break down proteins and combinations thereof. Exemplary additives include, without limitation, carbon sources, nitrogen sources, inorganic salt, organic acid, growth media, vitamins, minerals, acetic acid, amino acids, enzymes, lactase, protease, lactose, and the like. Also contemplated is the use of rose water. By way of example, without limitation, rose water may be added during fermentation to aid in breaking down milk proteins.

In one embodiment, the compositions of the present invention may further comprise milk. The weight fraction of the milk in the composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The compositions of the invention may be in liquid or dry form. The composition may comprise an aqueous suspension of components. This aqueous suspension may be provided as a concentrated stock solution which is diluted prior to application or as a diluted solution ready-to-use. Also, the composition may be a wettable powder, granules, pellet or colloidal concentrate. Such dry forms may be formulated to dissolve immediately upon wetting or dissolve in a controlled-release, sustained-release, or other time-dependent manner. Also, the composition may be in a dry form that does not depend upon wetting or dissolving to be effective.

The compositions of the present invention may also be formulated in a nutritional composition (e.g. foodstuff, food additive, dietary supplement, or feed additive). A nutritional composition of the present invention may include any of a variety of nutritional agents, which are well known in the art, including vitamins, minerals, essential and non-essential amino acids, carbohydrates, lipids, foodstuffs, dietary supplements, and the like. Thus, the compositions of the present invention may include fiber, enzymes and other nutrients. Preferred fibers include, but are not limited to: psyllium, rice bran, oat bran, corn bran, wheat bran, fruit fiber and the like. Dietary or supplementary enzymes such as lactase, amylase, glucanase, catalase and the like can also be included. Vitamins for use in the compositions of the present invention include vitamins B, C, D, E, folic acid, K, niacin, and the like. Typical vitamins are those, recommended for daily consumption and in the recommended daily amount (RDA).

The compositions of the present invention may be formulated in a pharmaceutical composition, where it is mixed with a pharmaceutically acceptable carrier for any type of administration route, selected according to the intended use.

In some embodiments, the combination of the invention may comprise at least one optional excipient. Non-limiting examples of suitable excipients include antioxidants, additives, diluents, binders, fillers, buffering agents, mineral salts, pH modifying agents, disintegrants, dispersing agents, flavoring agents, nutritive agents, oncotic and osmotic agents, stabilizers, preservatives, palatability enhancers and coloring agents. The amount and types of excipients utilized to form the combination may be selected according to known principles of pharmaceutical science.

In one embodiment, the excipient may include at least one diluent. Non-limiting examples of suitable diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lacitol, mannitol, malitol, sorbitol, xylitol, maltodextrin, and trehalose.

In another embodiment, the excipient may comprise a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, oligopeptides, and combinations thereof.

In another embodiment, the excipient may include a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may comprise a buffering agent. Representative examples of suitable buffering agents include, but are not limited to, MOPS, HEPES, TAPS, Bicine, Tricine, TES, PIPES, MES, Tris buffers or buffered saline salts (e.g., Tris buffered saline or phosphate buffered saline).

In a further embodiment, the excipient may include a disintegrant. Suitable disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth.

In yet another embodiment, the excipient may include a dispersion enhancer. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In a further embodiment, the excipient may include a lubricant. Non-limiting examples of suitable lubricants include minerals such as talc or silica; and fats such as vegetable stearin, magnesium stearate or stearic acid.

In still another embodiment, it may be desirable to provide a coloring agent. Suitable color additives include, but are not limited to, food, drug and cosmetic colors (FD&C), drug and cosmetic colors (D&C), or external drug and cosmetic colors (Ext. D&C).

The weight fraction of the excipient(s) in the combination may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the combination.

The compositions of the invention may include a cryoprotectant. Any cryoprotectant of microorganisms is suitable. Exemplary cryoprotectants include those made of a solution of water and sugar. Suitable sugars include, without limitation, dextrose mono-hydrate, fructose, galactose, bee honey, and others know in the art. Preferably, the cryoprotectant is a solution of water and bee honey.

The compositions of the invention include microoganisms that develop a protective shell during the production methods described herein. This protective shell preserves the viability of the probiotic association of these microorganisms when exposed to extreme conditions such as freezing, acidic environments, basic environments, and extended shelf-life. The compositions of the present invention are stable under various conditions as a liquid or dry form. Preferably, the compositions of the present invention are stable at room temperature.

II. Methods

The present invention encompasses methods of isolating microorganisms having a probiotic association, producing a starter material viably retaining the probiotic association, producing a dietary product with the viable probiotic association, and benefiting the health of a subject by administering a dietary product having the viable probiotic association. In regards to benefiting the health of a subject, the methods may be used to support or enhance a subject's health. The methods may be used to treat a subject harboring a condition that would benefit from probiotic therapy or that is at risk of developing a condition that would benefit from probiotic therapy.

In one aspect, methods of the invention include culturing microorganism strains of *Lactobacillus delbrueckii* subsp. *bulgaricus*, *Lactobacillus helveticus*, *Lactobacillus delbrueckii* subsp. *lactis*, *Streptococcus thermophillus*, and combinations thereof to produce a probiotic association, fermenting the probiotic association to produce a fermentation product, adding milk to the fermentation product, neutralizing the fermentation product to an optimal pH, and lyophilizing the fermentation product to produce a starter material. In some embodiments, the isolated microorganisms of the invention are cultured to produce a protective shell. This protective shell enhances viability of the microorganisms after exposure to extreme conditions, such as those experienced during production of a finished product, or long storage conditions.

Dietary Products

In another aspect, methods of the invention mixing starter material with an aqueous solution of milk and sugar to produce an aqueous starter material mixture, fermenting the starter material mixture to produce a fermentation product, and lyophilizing the fermentation product to produce a dietary product.

In one embodiment, the dietary product is combined with a nutritional supplement. Any suitable nutritional supplement known in the art that is compatible with the dietary product of the invention is contemplated. Exemplary nutritional supplements include, without limitation, oils, plant extracts, fibers, enzymes, honey, blueberry extract, papaya extract, cocoa, coffee, rose oil, lavender oil, cacao, dry extract of red geranium root, geranium oil, Ginseng, fibers, aloe vera, silymarine, extract from nettle root, pancreatic enzymes, bee pollen, others known in the art and combinations thereof.

The compositions and products of the present invention are shelf-stable for several months including at least about 1, 2, 3, 4, 5, 6, 7, 8, 9, 10, 11, 12, 13, 14, 15, 16, 17, 18, 19, 20, 21, 22 or more months. Shelf-stability includes viability of the microorganisms following exposure to extreme conditions. Such conditions include, without limitation, storage conditions, acidic pH, basic pH, freezing temperatures, hot temperatures, freeze-drying conditions, bactericide conditions, and bacteriostatic conditions, and other conditions harsh on viability of microorganisms.

Health

Methods of the invention include administering compositions to recipient subjects to support and promote health. Methods of the invention include administering compositions to recipient subjects to treat conditions including gastrointestinal and extraintestinal conditions.

Examples of gastrointestinal conditions include, without limitation, acute diarrhea, traveler's diarrhea, lactose intolerance, HIV-associated diarrhea, sucrose isomaltase deficiency, inflammatory bowel disease, pouchitis, carcinogenesis, enteral feeding associated diarrhea, antibiotic associated diarrhea, small bowel bacterial overgrowth, irritable bowel syndrome and conditions associated with enteropathogens. Such enteropathogens include, without limitation, *Helicobacter pylori, Campylobacter jejuni, Campylobacter coli, Staphylococcus aureus, Staphylococcus epidermidis, Streptococcus pyogenes, Streptococcus pneumoniae, Enterococcus faecalis, Haemophilus influenzae, Escherichia coli, Klebsiella pneumoniae, Enterobacter cloacae, Citrobacter freundii, Serratia marcescens, Pseudomonas aeruginosa* and *Pseudomonas maltophilia, Salmonella* sp., *Gasterophilus* sp., *Habronema* sp., *Crascia* sp., *Trichostrongvlus* sp., *Parascaris* sp., *Stroncrulus* sp., *Triodontophorus* sp., *Oxvuris* sp., *Stroncivloides* sp., *Anonlocephala* sp., *Paranonlocephala* sp., *Haemonchus* sp., *Hvostroncmulus* sp., *Spirocerca* sp., *Physoloptera* sp., viruses such as rotavirus, fungi such as *Candida albicans* and *Aspergillus fumigatus*, other species known or found to be associated with gastrointestinal conditions, and combinations of these species. Also contemplated are pathogens known in the art to cause gastrointestinal conditions such as those described in "Merck's Veterinary Manual" by Cynthia M. Kahn or "The Merck Manual of Diagnosis and Therapy" by Mark H. Beers, both incorporated herein by reference.

Also contemplated, is the use of microorganism compositions to treat extraintestinal conditions. Without being bound to a theory, extraintestinal conditions may be treated with microorganisms, microorganism extracts, or microorganism products that can stimulate multiple defense mechanisms including promotion of a nonimmunologic gut defense barrier. This barrier may inhibit translocation of potential pathogens and thus prevent infections of the blood stream and other tissues or organs. Another defense mechanism includes enhancing the intestine's immunologic barrier.

Examples of extraintestinal conditions include, without limitation, appendicitis, autoimmune disorders, multiple sclerosis, Alzheimer's disease, rheumatoid arthritis, celiac disease, diabetes mellitus, organ transplantation, periodontal disease, urogenital diseases (vaginal, urethral and perineal), sexually transmitted disease, HIV infection, HIV replication, surgical associated trauma, surgical-induced metastatic disease, sepsis, weight loss, anorexia, fever control, cachexia, wound healing, ulcers, gut barrier function, allergy, asthma, respiratory disorders, rhinovirus-associated diseases, otitis media, sinusitis, pulmonary disease, circulatory disorders, coronary heart disease, anemia, disorders of the blood coagulation system, renal disease, disorders of the central nervous system, hepatic diseases, constipation, ischaemia, nutritional disorders, osteoporosis, endocrine disorder, epidermal disorders, psoriasis, anthrax, metabolic diseases, weight gain, weight loss, dry eye syndrome, tired eye syndrome, presbyopia, acne, multiple organ failure due to drug addiction, and acute and chronic intoxications, as well as other conditions known in the art or yet to be discovered that may benefit from treatment with microorganisms, microorganism extracts, or microorganism products.

The following examples are simply intended to further illustrate and explain the present invention. The invention, therefore, should not be limited to any of the details in these examples.

Definitions

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

As used herein, "administering" is used in its broadest sense to mean contacting a subject, surface, liquid, or environment with a composition of the invention.

The term "co-culture" refers to a culture of microorganisms that includes at least two microorganism of the present invention, described herein.

The phrase "fermentation product" refers to a mixture including at least one microorganism, expression products of the microorganism(s), substances produced by the microorganisms, and extracts of the microorganisms.

The phrase "finished product" refers to a mixture including a fermentation product. The finished product may include additional additives.

As used herein, "subject" refers to a living organism having a central nervous system. In particular, subjects include, but are not limited to, human subjects or patients and companion animals. Exemplary companion animals may include domesticated mammals (e.g., dogs, cats, horses), mammals with significant commercial value (e.g., dairy cows, beef cattle, sporting animals), mammals with significant scientific values (e.g., captive or free specimens of endangered species), or mammals which otherwise have value. Suitable subjects also include: mice, rats, dogs, cats, ungulates such as cattle, swine, sheep, horses, and goats, lagomorphs such as rabbits and hares, other rodents, and primates such as monkeys, chimps, and apes. Subjects may be of any age including new born, adolescence, adult, middle age, or elderly.

The term "probiotic association" refers to the co-existence of more than one microorganism in a culture, whereby the microorganisms produce a probiotic benefit. Such probiotic benefits may include, without limitation, health benefit to a subject that injests products containing the co-existing microorganisms or fermentation products or metabolites thereof.

The term "pharmaceutical composition" refers to a preparation of one or more compositions of the invention with additional components such as physiologically suitable carriers and excipients. The purpose of a pharmaceutical composition is to facilitate administration of a composition to a recipient subject.

The term "physiologically acceptable carrier" refers to a carrier or a diluent that does not cause significant irritation to a subject and does not abrogate the biological activity and properties of the administered composition.

The term "excipient" refers to an inert substance added to a pharmaceutical composition to further facilitate administration of a composition. Examples, without limitation, of excipients include calcium carbonate, calcium phosphate, various sugars and types of starch, cellulaose drivatives, gelatin, vegetable oils and polyethylene glycols. Techniques for formulation and administration of pharmaceutical compositions are known in the art and may be found in "Remington's Pharmaceutical Sciences," Mack Publishing Co., Easton, Pa., latest edition, which is incorporated herein by reference.

As various changes could be made in the above compositions and methods without departing from the scope of the invention, it is intended that all matter contained in the above description and in the Examples given below, shall be interpreted as illustrative and not in a limiting sense.

EXAMPLES

The following examples illustrate various iterations of the invention.

Example 1

Characterization of the Probiotic Association

All analyses with regard to the species and strain composition of the association of probiotic microorganisms, whose results are discussed below, have been carried out in the DNA Analysis Lab of ELBI Bulgaricum EAD, Sofia, Bulgaria. Tests have been carried out for two samples identified formally as IN1 and IS1.

Establishing species composition. Species affiliation of the rods contained in the probiotic association of microorganisms, isolated from spring water from a source in Mountain Stara Planina, has been established through the ARDRA method (amplified ribosomal DNA restriction analysis) following Giraffa et al., J. Appl. Microbiol. 1998, 85, 918-924. The species affiliation of the cocci forms in the same probiotic association has been established by the species-/genus-specific PCR following Lick et al., System. Appl. Microbio. 1996, 19, 74-77, Nomura et al., Appl. Eviron. Microbiol. 2002, 68(5), 2209-2213, and Ke et al., J. Clin. Microbiol. 1999, 37, 3497-3503. *Lactobacillus delbrueckii* ssp. *bulgaricus* ATCC 11842, *Lactobacillus helveticus* DSM20075, *L. delbrueckii* ssp. *lactis* DSM 20072, *Streptococcus thermophilus* DSM 20617; *Lactococcus lactis* ssp. *lactis* DSM 20481 and *Enterococcus faecalis* LMG 2937 have been used as reference cultures.

Establishing the strain composition of the samples. Distinguishing between the various strains in the isolates from the samples is essential for the macrorestriction analysis using the Pulsed Electrophoresis of the CHEF-DR II BioRad system. For the restriction analysis of the genomic DNA the enzymes SmaI and XhoI were used for the cocci and the rods respectively.

Quantitative values for the cocci and rods in Sample IN1: The estimated number of cocci and rods in sample IN1 taken from spring water in April 2011 was based on the number of grown colonies from sample IN1 in mediums M17 and MRS; the number of cocci and rods was estimated to be 4.6×

$10^7$ cfu/g and $3.5 \times 10^7$ cfu/g respectively. All the cocci isolates belong to the *Streptococcus thermophilus* species, while the rods belong to the *Lactobacillus helveticus, Lactobacillus delbrueckii* ssp. *bulgaricus* and *Lactobacillus delbrueckii* ssp. *lactis* species.

Strain composition of sample IN1: Sample IN1 gives the genetic profile of seven isolates of *Streptococcus thermophilus*, designated formally as i21, i22, i24, i26, i31, i32 and i34. In total, five genetic profiles were established, corresponding to at least five strains of *Str. thermophilus* in the same sample. Pairs (i21 and i24) and (i32 and i34) were found to have the same profiles, while isolates i22, i26 and i31 have independent profiles. The MRPs of these isolates are shown in FIG. 1, and the size of the resultant restriction fragments is shown in FIGS. 3-7.

Figure 2:
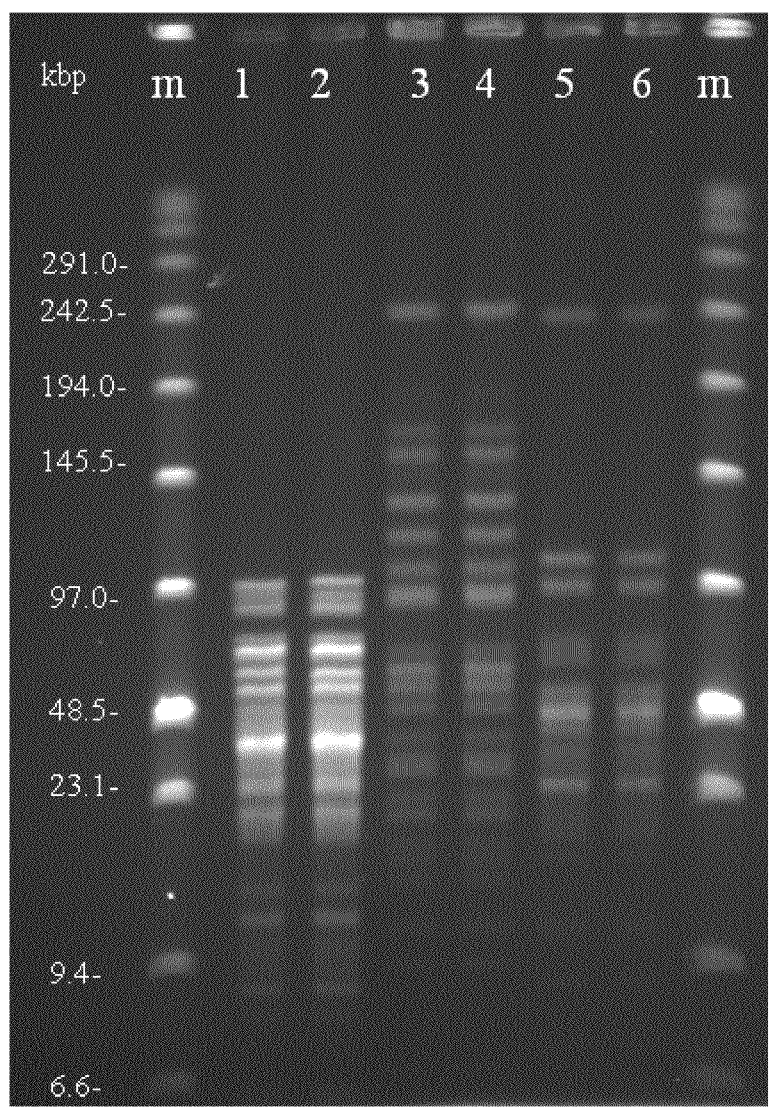
FIG. 2 shows the macrorestriction profiles of isolates of *Lactobacillus helveticus, Lb. delbrueckii* ssp. *bulgaricus* and *Lb. delbrueckii* ssp. *lactis,* of the probiotic association. Specifically.
Figure 3:
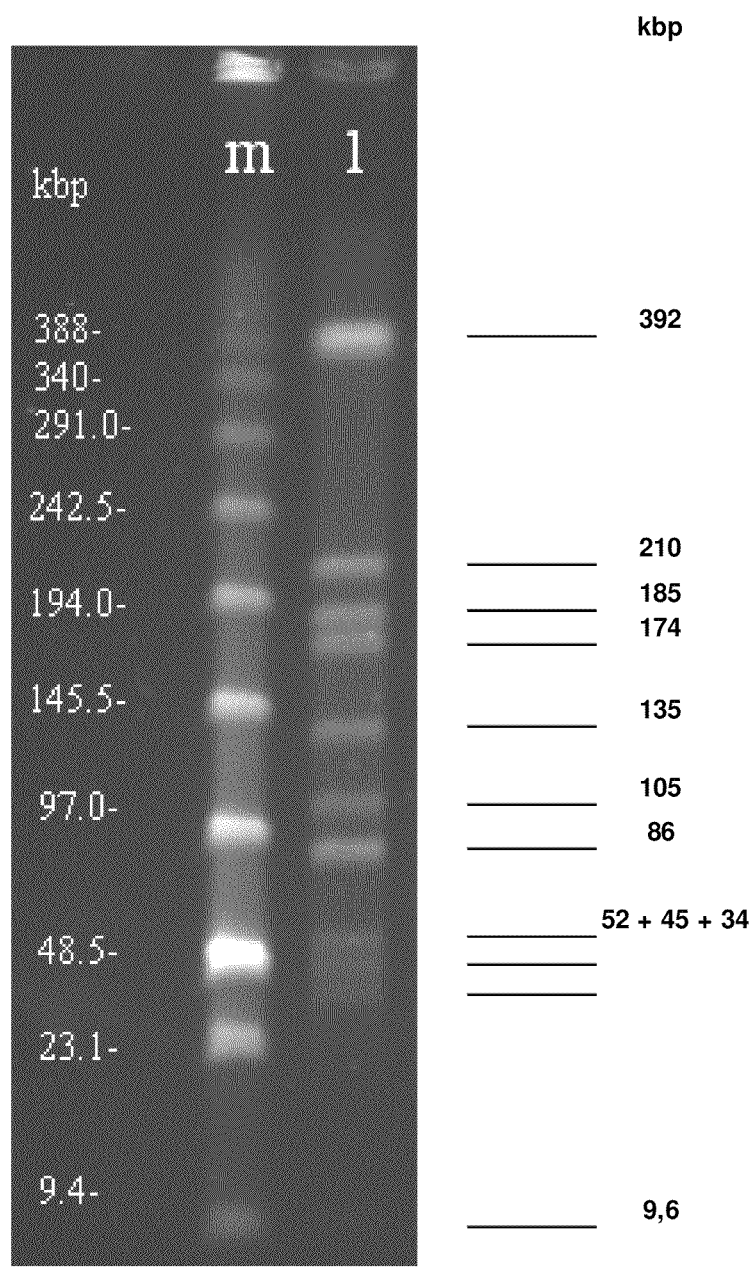
FIG. 3 shows a restriction fragment of an isolate of *Streptococcus thermophilus,* corresponding to the strain of *Streptococcus thermophillus* DWT5 registered in CCM under no. 7993. Specifically.
Figure 4:
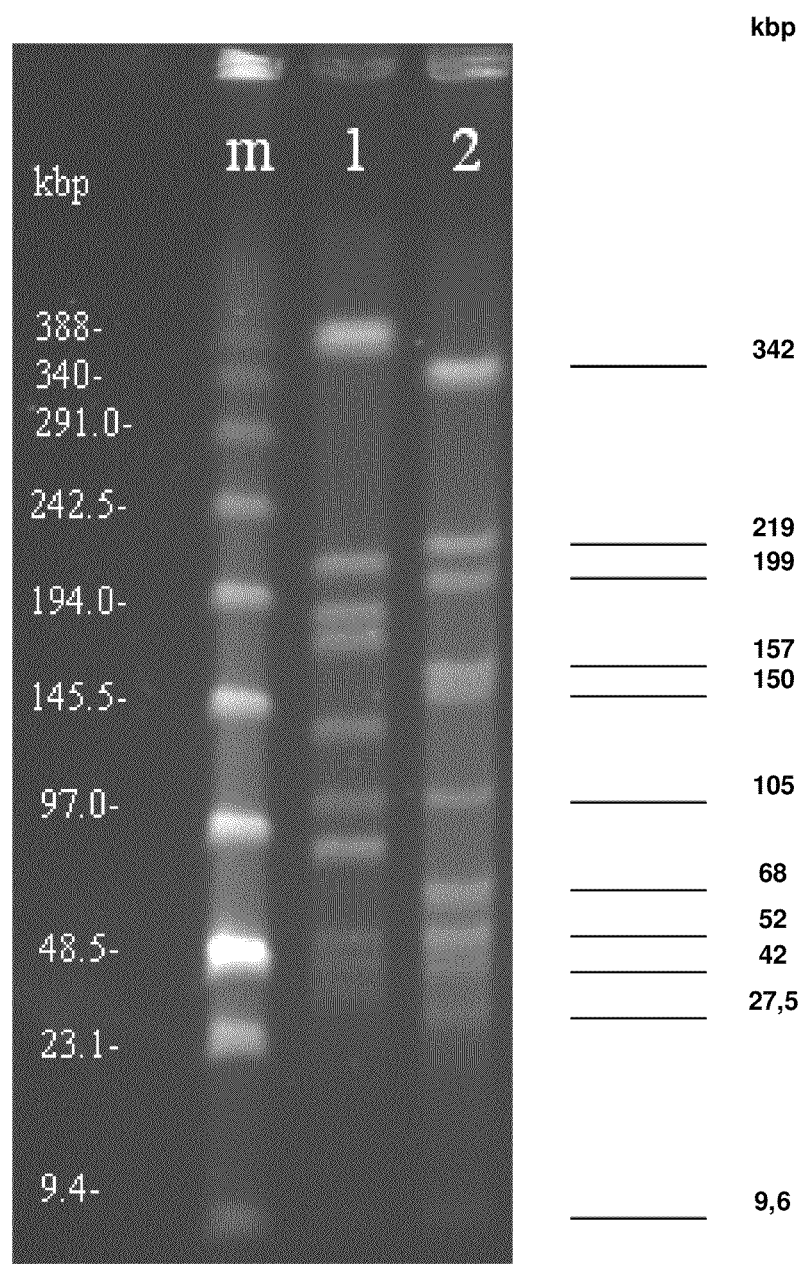
FIG. 4 shows a restriction fragment of an isolate of *Streptococcus thermophilus,* corresponding to the strain of *Streptococcus thermophillus* DWT4 registered in CCM under no. 7992. Specifically.
Figure 5:
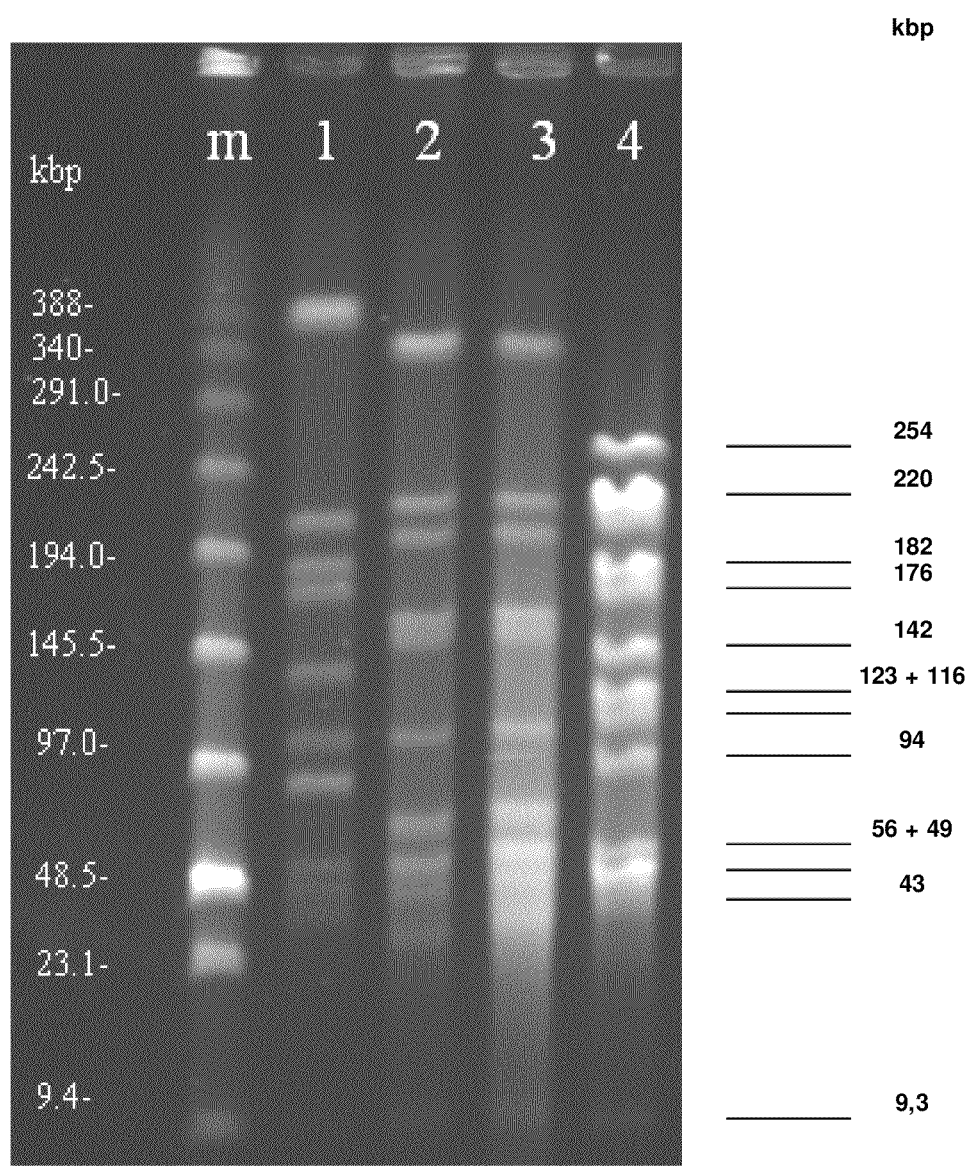
FIG. 5 shows a restriction fragment of an isolate of *Streptococcus thermophilus,* corresponding to the strain of *Streptococcus thermophillus* DWT6 registered in CCM under no. 7994. Specifically.
Figure 6:
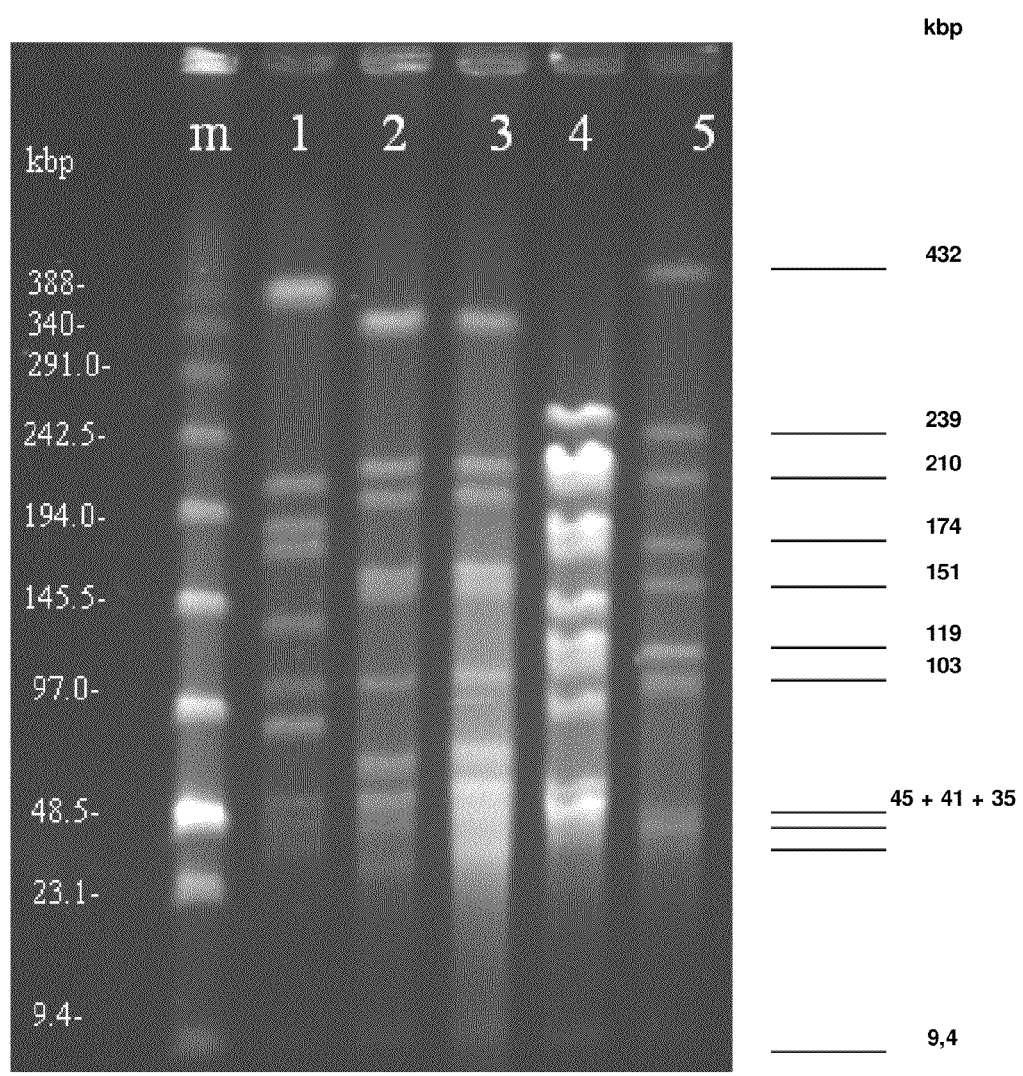
FIG. 6 shows a restriction fragment of an isolate of *Streptococcus thermophilus,* corresponding to the strain of *Streptococcus thermophillus* DWT8 registered in CCM under no. 7996. Specifically.
Figure 7:
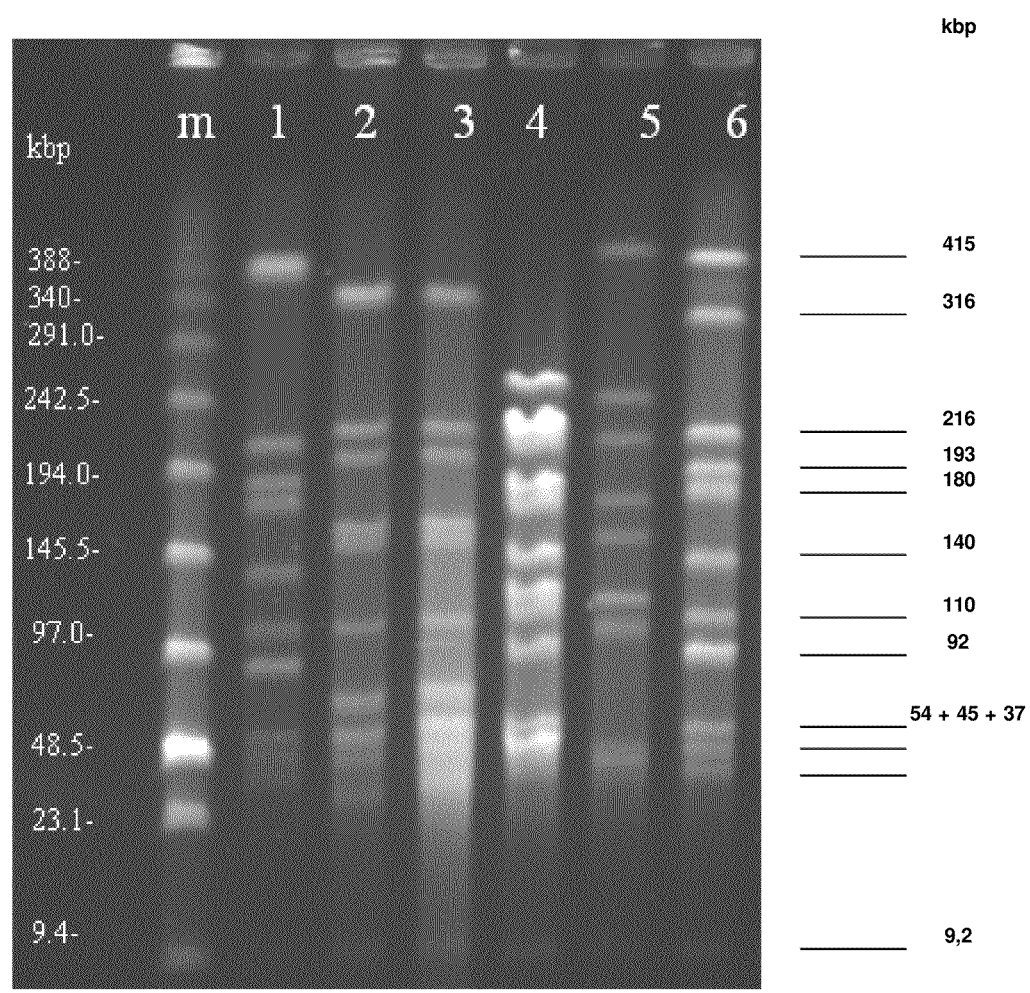
FIG. 7 shows a restriction fragment of an isolate of *Streptococcus thermophilus*, corresponding to the strain of *Streptococcus thermophillus* DWT7 registered in CCM under no. 7995. Specifically.
Figure 8:
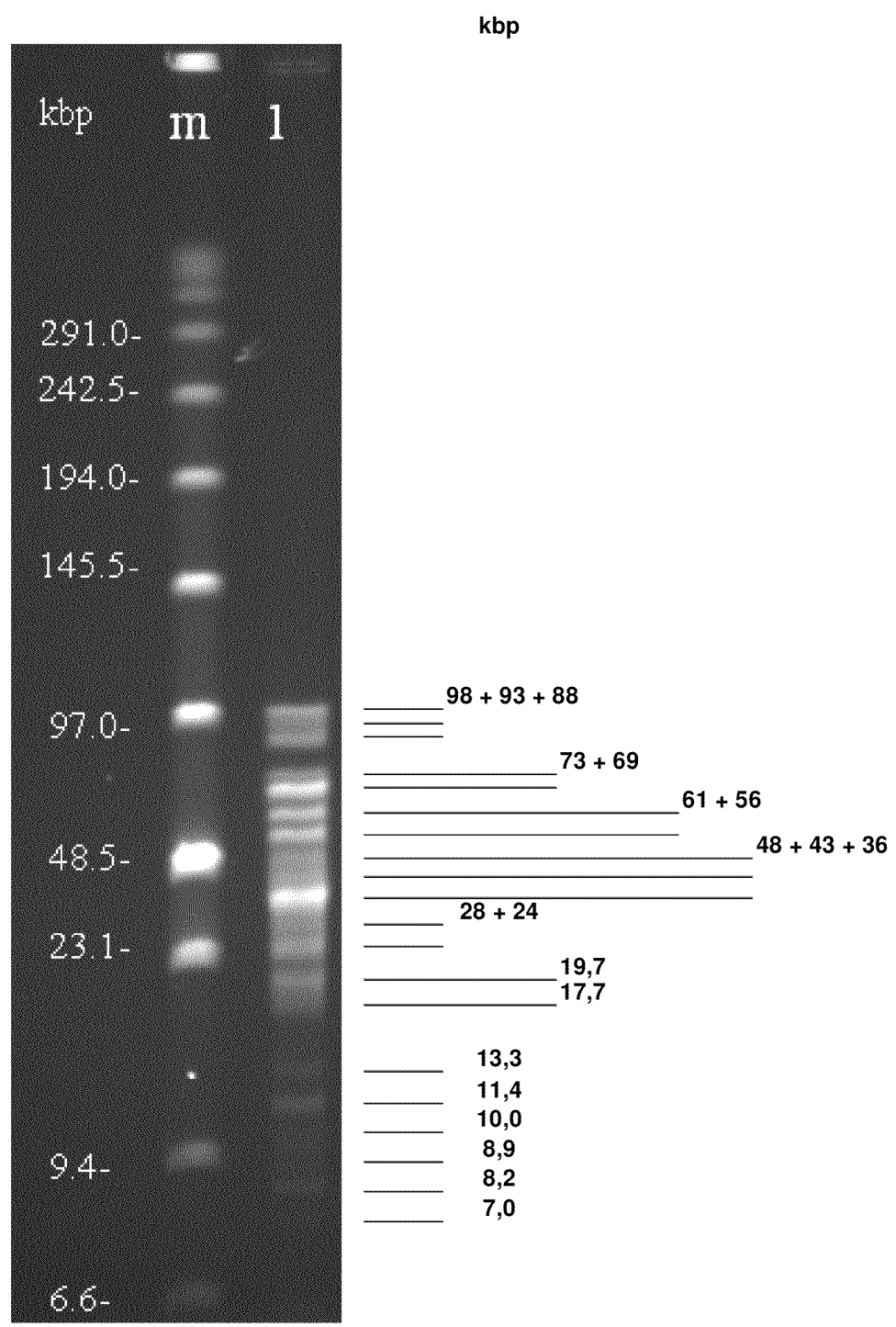
FIG. 8 shows a restriction fragment of an isolate of *Lactobacillus helveticus*, corresponding to the strain of *Lactobacillus helveticus* DWT2 registered in CCM under no. 7993. Specifically.
Figure 9:
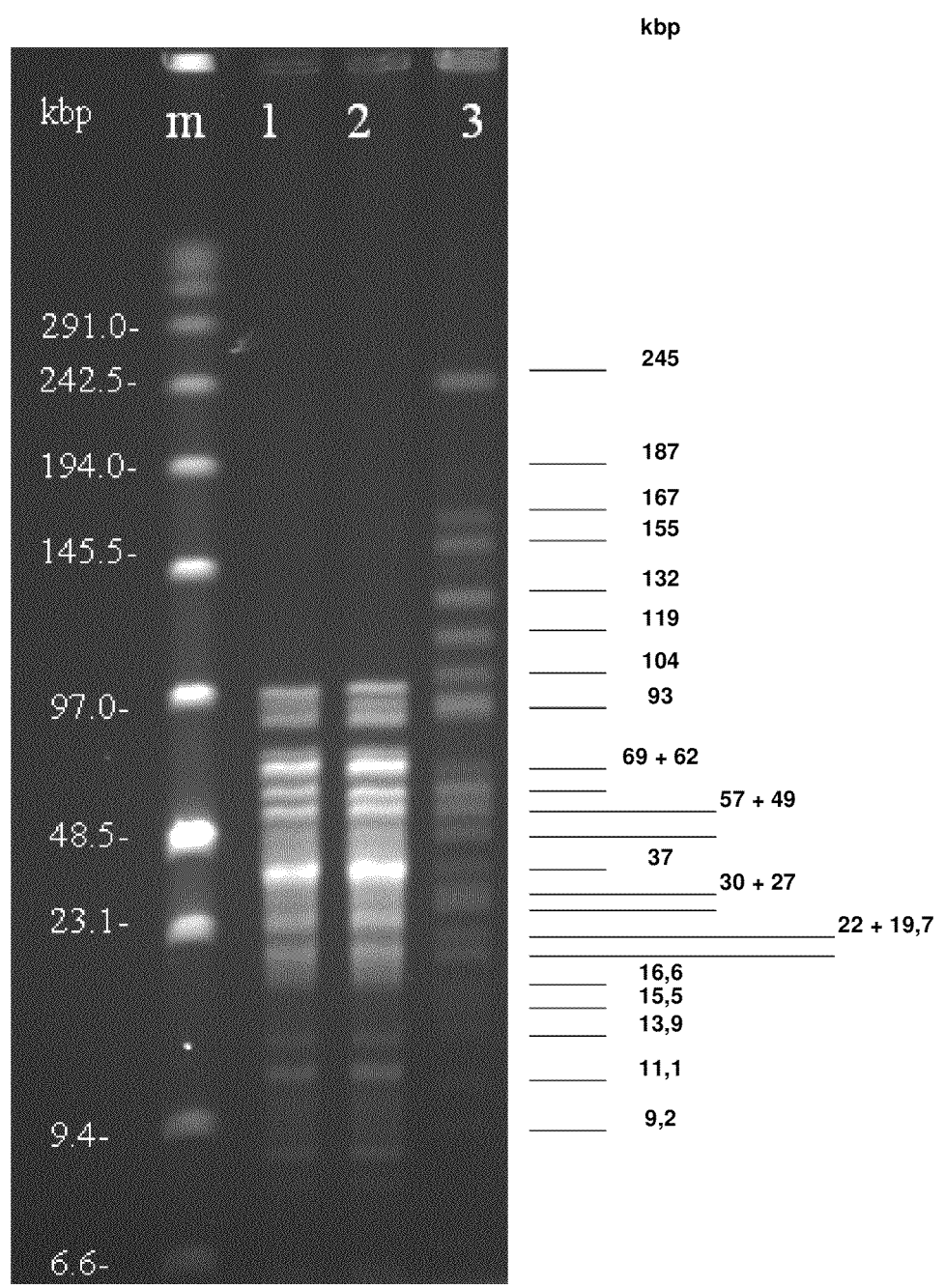
FIG. 9 shows a macrorestriction profile of genomic DNA of an isolate of *Lactobacillus delbrueckii* subsp. *bulgaricus*, corresponding to the strain *Lactobacillus delbrueckii* subsp. *bulgaricus* DWT1, registered in CCM under no. 7992. Specifically.
Figure 10:
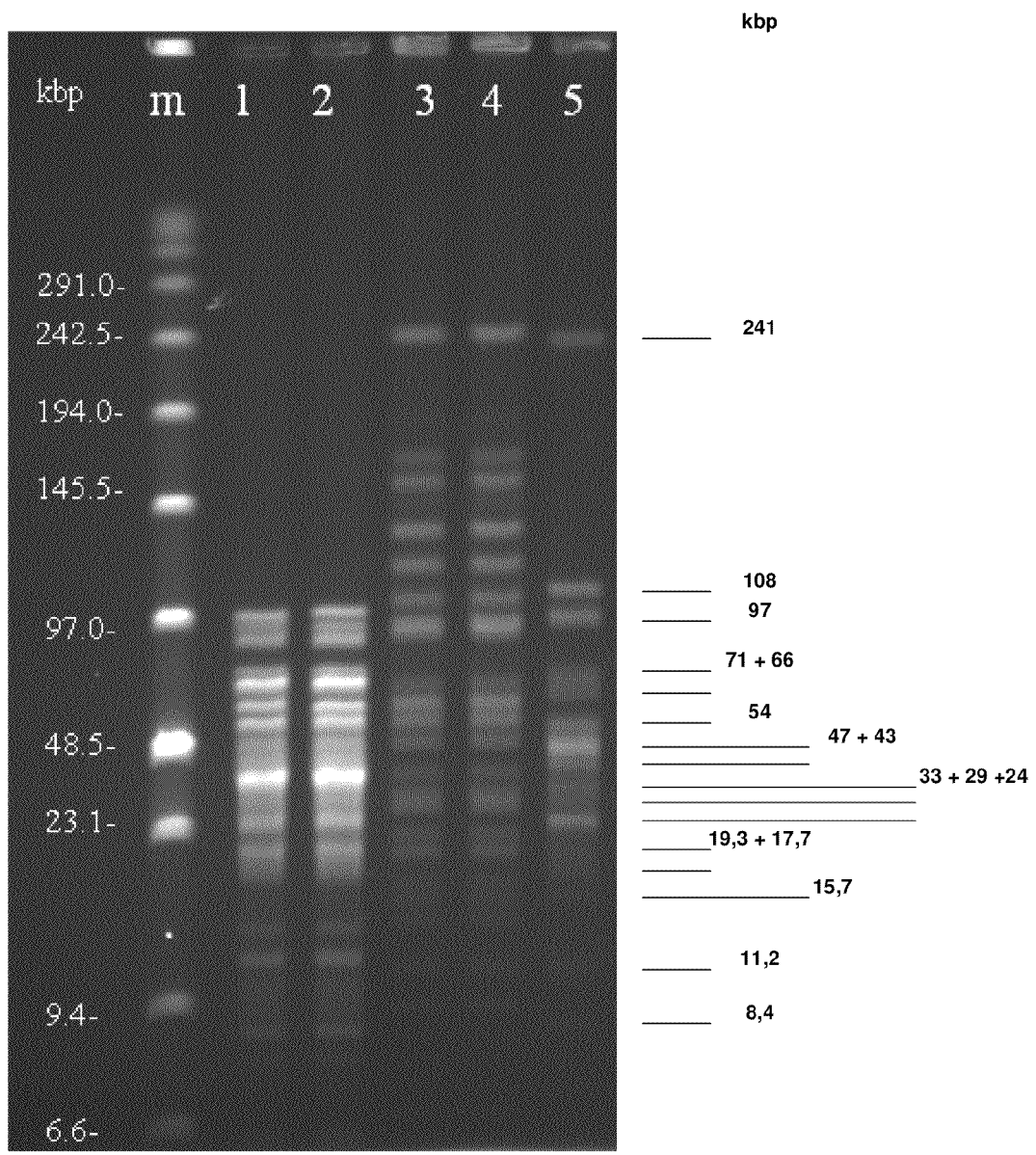
FIG. 10 shows a macrorestriction profile of genomic DNA of an isolate of *Lactobacillus delbrueckii* subsp. *lactis*, corresponding to the strain *Lactobacillus delbrueckii* subsp. *lactis* DWT3, registered in CCM under no. 7994. Specifically.

For the same sample, the genetic profile of the following isolates was established, designated formally as *Lactobacillus helveticus* i1m and i5m, *Lactobacillus delbrueckii* ssp. *bulgaricus* i2m and i4s and *Lactobacillus. delbrueckii* ssp. *lactis* i3L and i7L. In total, three profiles were established, matching each pair of isolates of the three types of lactobacilli. The MRPs of the lactobacilli isolates in sample IN1 are shown in FIG. 2, and the size of the resultant restrictive fragments is detailed in FIGS. 8-10.

Quantitative values concerning the cocci and rods in Sample IS1: For confirming the microbial content of Sample IS1 taken from spring water in March 2010, the estimate of the number of cocci and rods was based on the number of grown colonies from Sample IS1 in environments M17 and MRS as with sample IN1 above; the number of cocci and rods was estimated to be $4.9 \times 10^7$ cfu/g and $5.6 \times 10^7$ cfu/g, respectively. All the cocci isolates belong to the *Streptococcus thermophilus* genus, while the rods belong to the *Lactobacillus helveticus, Lactobacillus delbrueckii* ssp. *bulgaricus* and *Lactobacillus delbrueckii* ssp. *lactis* species.

Strain composition of sample IS1: Sample IS1 provided the genetic profile of six isolates of *Streptococcus thermophilus*. A total of five genetic profiles have been found and they correspond to the five strains of *Streptococcus thermophilus*. These five genetic profiles are identical to the genetic profiles of isolates i21, i22, i26, i31 and i32 of *Streptococcus thermophilus* in sample IN1. The findings for sample IS1 also identify the genetic profile of six isolates of *Lactobacillus helveticus, Lactobacillus delbrueckii* ssp. *bulgaricus* and *Lactobacillus delbrueckii* ssp. *lactis*. A total of three genetic profiles have been obtained, identical to the genetic profiles of isolates i1m of *Lactobacillus helveticus*, i2m of *Lactobacillus delbrueckii* ssp. *Bulgaricus* and i3L of *Lactobacillus delbrueckii* ssp. *lactis* in sample IN1.

The identical results with regard to the composition of the probiotic association obtained by studying the two different samples taken within a time span of one year from one and the same natural water source—a spring in Mountain Stara Planina, indicate unequivocally that these strains of probiotic microorganisms can live independently in spring water and multiply together.

Example 2

Proving the Water Origin of the Association

In order to exclude contamination from sources near to the springs, parallel studies of the microbial content were conducted of the samples isolated from the moss on the tree which is four metres away (Sample P1), from the grass next to the spring (Sample P2) and the underwater algae in the spring (Sample P3) in September 2011.

The methods for establishing the number of lactic acid bacteria, the species and strain composition of the samples, are identical to the methods used in analysing sample IN1 as in Example 1.

Species composition of samples P1, P2 and P3. The species composition of the different samples and their numbers per type of microorganisms are shown in Table 2. Within the cocci group the samples have been found to contain *Enterococcus* sp. and *Streptococcus thermophilus*, from the lactobacilli—only *Lactobacillus delbrueckii* ssp. *lactis*. *Lactobacillus delbrueckii* ssp. *bulgaricus* or *Lactobacillus helveticus* have not been detected.

TABLE 2

Species composition and number of microorganisms (cfu/g) in said samples.

| Sample | *Enterococcus* sp. | Str. *Thermophilus* | *Lactobacillus delbrueckii* ssp. *lactis* | Other, not lactic acid bacteria | *Lactobacillus delbrueckii* ssp. *bulgaricus* | *Lactobacillus helveticus* |
|---|---|---|---|---|---|---|
| P1 | $7.2 \times 10^6$ | $3.5 \times 10^6$ | — | — | — | — |
| P2 | $1.9 \times 10^5$ | $3.8 \times 10^4$ | $5.8 \times 10^4$ | $2.3 \times 10^4$ | — | — |
| P3 | $6.8 \times 10^5$ | $2.0 \times 10^6$ | $1.6 \times 10^5$ | $3.5 \times 10^3$ | — | — |

Strain Composition of the Samples

Figure 11:
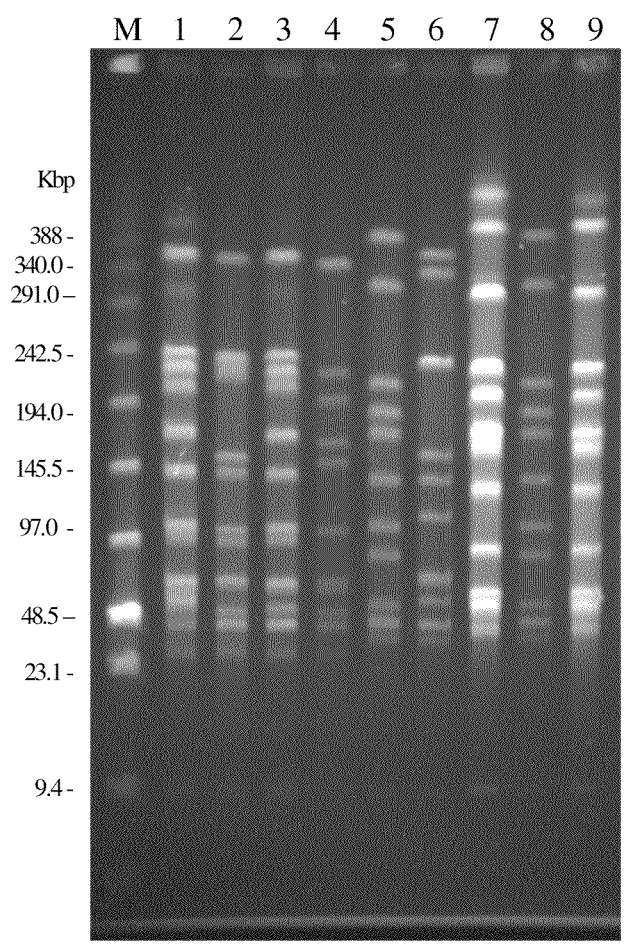
FIG. 11 shows a genetic profile of isolates of *Streptococcus thermophillus* from samples taken near the water source (tree and grass moss nearby). Specifically.

Strains of *Streptococcus thermophilus*. According to genetic profiling, at least two strains of *Streptococcus thermophilus* were found in sample P1, represented by isolates Pк1/1 and Pк1/2 (Pк1/3 is identical to Pк1/1) (FIG. 11, tracks 7-9). Two strains of *Streptococcus thermophilus* were also detected in sample P2, represented by isolates Pк2/1 and Pк2/2 (FIG. 11, tracks 5 and 6). In sample P3, four isolates of *Streptococcus thermophilus* were analysed, all of which showed profiles identical to the industrial strain LBB.TN1 (the strain is owned by ELBI Bulgaricum EAD and the profile is not presented here). Samples P1 and P2 share the profile of the strain *Streptococcus thermophilus* represented by isolates Pк1/2 and Pк2/1, respectively (FIG. 11, tracks 8 and 5). Compared to the profiles of the isolates of *Streptococcus thermophilus* in sample IN1, as shown in Example 1 above, the isolates of samples P1, P2, and P3 are different and do not coincide with earlier isolates.

Figure 12:
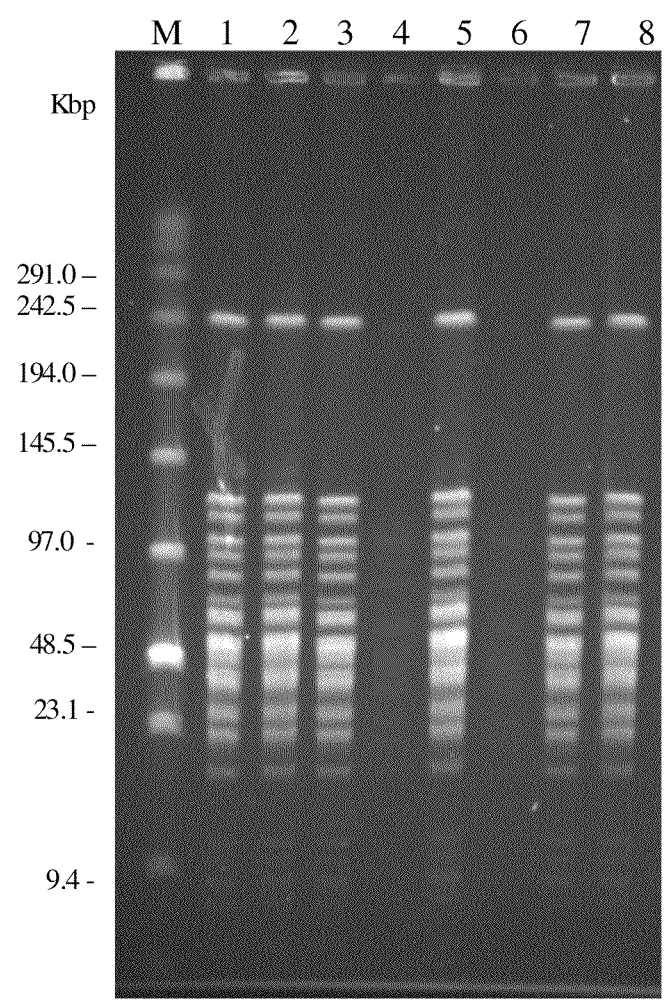
FIG. 12 shows a genetic profile of isolates of *Lactobacillus delbrueckii* subsp. *lactis* from samples taken near the water source (nearby grass and algae underwater). Specifically.
Figure 13:
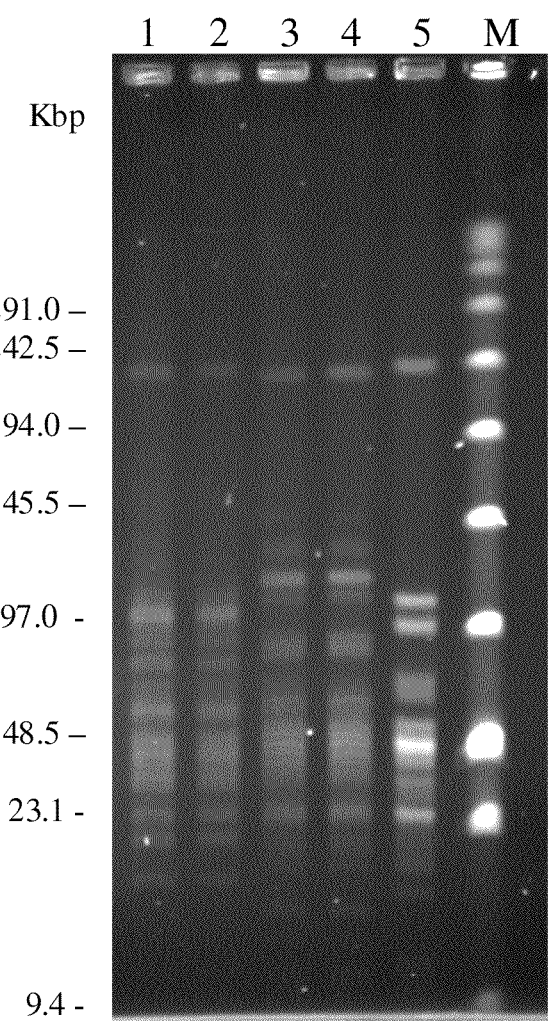
FIG. 13 shows a genetic profile of isolates of *Lactobacillus delbrueckii* subsp. *lactis* from samples taken near the water source (nearby grass and algae underwater) compared to a genetic profile of an isolate from the spring water. Specifically.
Figure 14:
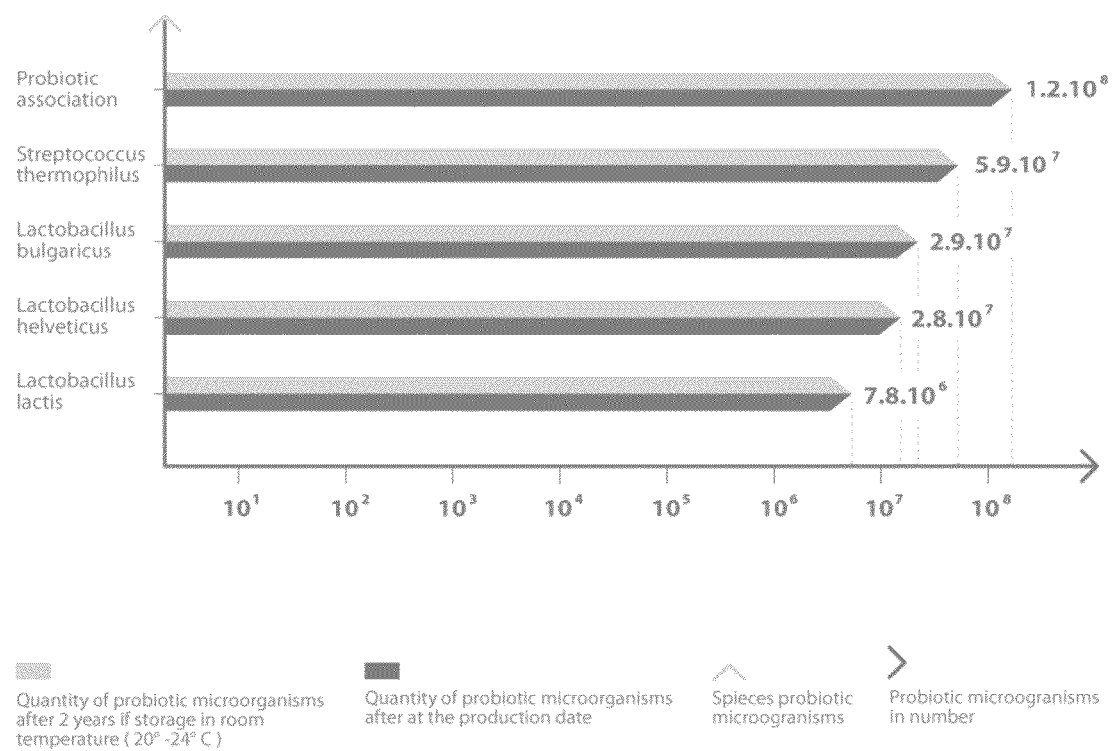
FIG. 14 graphically illustrates the viability of the probiotic microorganisms by storage in room temperature (20°-24° C.)
Figure 15:
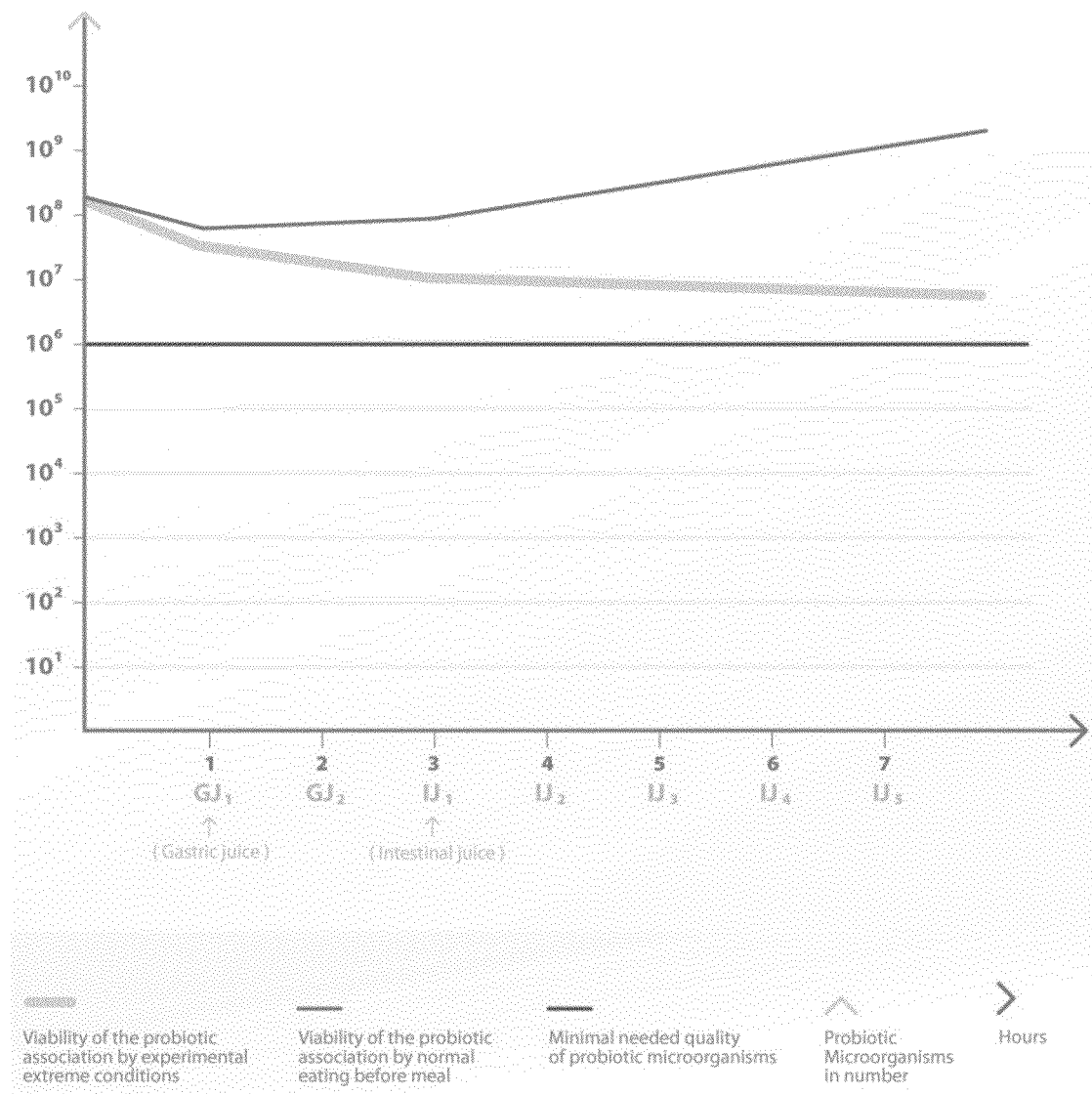
FIG. 15 graphically illustrates the viability of the probiotic association in the gastric intestinal track; and, FIG. 16 graphically illustrates the antimicrobial activities of the probiotic association.
Figure 16:
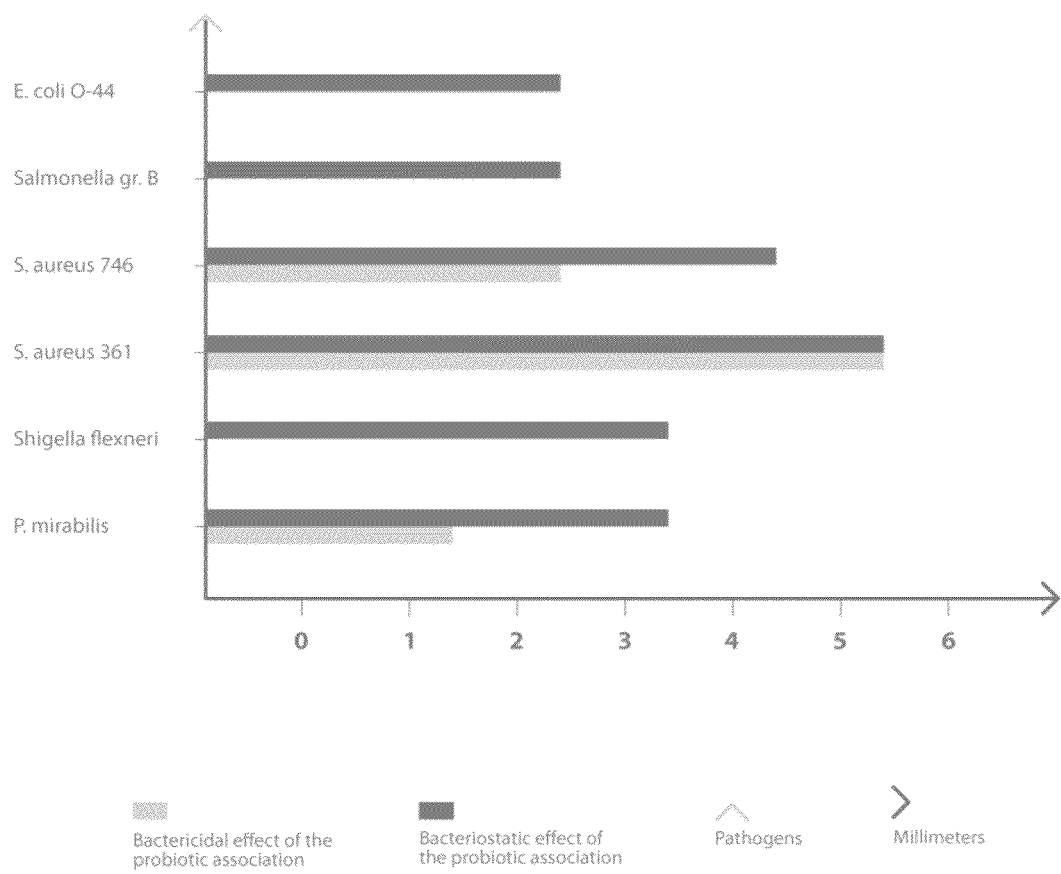

Strains *Lactobacillus delbrueckii* ssp. *Lactis*. Samples P2 and P3 show presence of at least two strains of *Lactobacillus delbrueckii* ssp. *Lactis* common for both samples. One of the profiles can be seen clearly and includes isolates Pp3/1, Pp3/3, Pp3/5, Pp2/2, Pp2/4 and Pp2/5 (FIG. 12). The profile of the second strain, *Lactobacillus delbrueckii* ssp. *lactis*, is better characterised by the second analysis, which showed the identity of isolates Pp3/6 and Pp2/3 (FIG. 13, tracks 1 and 2). Neither of the profiles of the strains *Lactobacillus delbrueckii* ssp. *lactis* matches the profile of *Lactobacillus delbrueckii* ssp. *lactis* i3L in sample IN1, as shown in Example 1 (FIG. 13, track 5), which indicates that the strains contained in samples P2 and P3 differ from the strains isolated from the spring water.

The results of the tests on microorganisms found in the moss on the tree, the grass around the spring, and the algae in the spring, differ from those found in the spring water and provide further proof that the probiotic association of microorganisms isolated from the natural water source, has not resulted from contamination.

Example 3

Obtaining a Dietary Dairy Product Containing a Probiotic Association

In order to obtain a dietary dairy product with a starter culture containing the probiotic association detailed in Examples 1 and 2 above, the microorganisms isolated from the spring water are captured and multiplied with a view of obtaining biomass. For this purpose 1.0 litre regular and pasteurized cow's milk with 3.6% fat was cultured with 0.5 litre water taken directly from the spring. A container with the milk and the spring water was placed in a water jacket at temperatures of 43° C. for 40 hours, at the end of which period white soft-textured biomass was released onto the surface. During fermentation, the microorganisms absorb lactose creating an envelope glycoprotein shell. This shell allows the microorganisms to remain viable after exposure to extreme conditions. Also, this shell extends the shelf-life of products containing these microorganisms.

The biomass was then used to obtain a starter culture, for which purpose a 10% water solution of dry regular whole cow's milk was sterilized at 121° C. for 15 minutes and cooled down to 45° C. and for each 10.0 litres, 3.0 g of the above-mentioned biomass was added. The mixture was left to ferment for 12 hours at a temperature of 43° C. in order to produce liquid culture. Then, another 10% water solution of dry regular whole cow's milk was prepared, which was sterilized at 121° C. for 15 minutes and then left to cool to 45° C. And, for each 6.0 litres of this solution 0.1 litre liquid culture of spring water was added. The mixture was neutralized by a 10% sodium hydroxide solution until the optimal pH from 4.6 to 4.7 was reached and the resultant fermentation product was subjected to lyophilisation for 48 hours. This dry product formed the starter culture for obtaining dietary dairy products.

In order to obtain a dry dietary dairy product, a 10% water solution of dry regular whole or non-fat cow's milk was sterilized at 95° C.-96° C. for 30 minutes, then cooled down to 45° C. and neutralized by a 10% sodium hydroxide solution until a pH of 6.6-6.7 was reached. Then a water sugar solution was prepared in a 1:1 ratio and heated until boiling, left to cool down and added to the water solution of the milk in a 10:1 ratio of the milk and sugar solution. Next, 3.0 g dry starter culture was added to each 5.0 of the mixture, obtained as in Example 3 above. Fermentation occurred in the next 12 hours at 43° C.-45° C. and the resultant product was subjected to lyophilisation for 48 hours. The latter involved freezing at temperatures of −41° C. and sublimation until a temperature of 31° C. was reached. The obtained products were kept at ambient temperature.

Example 4

Survival Rate after Freeze-Drying

The survival rate of the probiotic association of strains of lactic acid microorganisms after freeze-drying was carried out using the same methods of determining the species composition and number of microorganisms in the samples applied in Example 1. The survival rate during the process of freeze-drying was determined by analyzing the number of lactic acid bacteria and the species composition in a liquid sample (TI) and dry sample (VI). The TI represents the fermentation product for obtaining the ingredients of probiotic products, immediately before freeze-drying. The sample was obtained in October 2011 out of starter dry culture, extracted from spring water, taken in April 2011. The VI, on the other hand, was produced through freeze-drying the TI.

Sample contents. The data about the species composition and numbers of the separate groups of microorganisms in each sample are summarized in Table 3 below. From the Cocci group the following are found in the sample *Streptococcus thermophilus*, and from the group of the lactic acid the presence of the following is established-*Lactobacillus delbrueckii* ssp. *lactis*, *Lactobacillus delbrueckii* ssp. *bulgaricus* and *Lactobacillus helveticus*.

TABLE 3

| Sample | *Streptococcus thermophilus* | *Lactobacillus delbrueckii* ssp. *lactis* | *Lactobacillus delbrueckii* ssp. *Bulgaricus* | *Lactobacillus helveticus* |
|---|---|---|---|---|
| TI - liquid (cfu/ml) | $9.6 \times 10^7$ | $2.2 \times 10^7$ | $6.1 \times 10^8$ | $2.5 \times 10^8$ |
| VI - dry (cfu/g) | $4.6 \times 10^7$ | $6.1 \times 10^6$ | $1.4 \times 10^7$ | $1.4 \times 10^7$ |

As it can be seen in Table 3, the number of lactic acids [Inventor: Is "lactic acids" referring to lactic acid microorganisms here?] in the liquid sample is considerable with a significant preponderance of *Lactobacillus delbrueckii* ssp. *bulgaricus*, which in lactic environment may easily reach up to $10^9$ cfu/ml. The number of *Streptococcus thermophilus* is about up to $10^8$ cfu/ml, which is the usual number in lactic environments, but is lower than that commonly obtained in cultivation under controlled pH (above $10^9$ cfu/ml). In the dry sample the content of rods and cocci has slightly decreased, but has still preserved a high level. Taking into consideration the high sensitivity of these species of lactic acid microorganisms to freeze-drying, the results of the research irrefutably indicate that the technological process of freezing and freeze-drying have been conducted successfully and that the lactobacilli and cocci are preserved live and corresponding to the quantitative requirements for probiotic products.

Example 5

Survival Rate during Storage at Room Temperature (20°-24° C.)

In order to prove the survival rate of microorganisms in time, research has been done into the numbers and species composition of lactic acid bacteria in samples IN1, IV1 and IS1 from dry dietary products, obtained through a method according to the invention. Sample IN1 was obtained in May, 2011 from a dry starter culture, extracted from spring water taken in April 2011; Sample IV1 was obtained in November, 2011 from a dry starter culture, obtained from spring water taken in April 2011 and Sample IS1 was obtained in March 2010 from a dry starter culture, obtained from spring water taken in March 2010. All samples after being obtained were stored and kept at room temperature 18° C.-24° C.

Species composition in samples IN1, IV1 and IS1. In all three samples the measurement of the numbers was done in terms of the number of grown colonies after development in a culture of tenfold diluted dry product in mediums M17 and MRS. The number of cocci and rods were as follows:

Sample IN1—$4.6 \times 10^7$ cfu/g cocci and $3.5 \times 10^7$ cfu/g rod-shaped.
Sample IV1—$5.9 \times 10^7$ cfu/g cocci and $6.5 \times 10^7$ cfu/g rod-shaped.
Sample IS1—$4.9 \times 10^7$ cfu/g коки and $5.6 \times 10^7$ cfu/g rod-shaped.

All isolated cocci belong to the species of *Streptococcus thermophilus*, whereas the rod-shaped ones belong to *Lactobacillus helveticus, Lactobacillus delbrueckii* ssp. *bulgaricus* and *Lactobacillus delbrueckii* ssp. *lactis*.

The species affiliation of the samples and the numbers of the separate groups of microorganisms in them (cfu/g), as well as the ratio of the bacteria species in the samples are presented in Table 4 below.

TABLE 4

| Sample | *Streptococcus thermophilus* | *Lactobacillus delbrueckii* ssp. *lactis* | *Lactobacillus delbrueckii* ssp. *bulgaricus* | *Lactobacillus helveticus* | Total number of lactic acid microorganisms |
|---|---|---|---|---|---|
| IN1 | $4.6 \times 10^7$ | $6.1 \times 10^6$ | $1.4 \times 10^7$ | $1.4 \times 10^7$ | $8 \times 10^7$ |
| IV1 | $5.9 \times 10^7$ | $7.8 \times 10^6$ | $2.9 \times 10^7$ | $2.8 \times 10^7$ | $1.2 \times 10^8$ |
| IS1 | $4.9 \times 10^7$ | $6.5 \times 10^6$ | $2.7 \times 10^7$ | $2.6 \times 10^7$ | $1.1 \times 10^8$ |

The results of the analyses show that the association of probiotic strains of lactic acid microorganisms, isolated from spring water, stored for 22 months in sample IS1 (from March, 2010 to January, 2012) at a temperature of 20° C.-24° C., contains live, viable microorganisms in quantities close to the quantity in sample obtained later (IV1). Therefore, the viability of the probiotic association of lactic acid microorganism strains, isolated from spring water, is preserved for long periods of storage at room temperature. The latter is of paramount importance for dietary products on the market, manufactured with technology as per the invention.

Example 6

Rate of Survival in the Gastrointestinal Tract

The rate of survival of microorganisms is determined through treatment of rehydrated products, obtained from a starter culture, with artificial gastric and intestinal juice. This experimental method, which was aimed at simulating the transition of the microorganisms through the gastric-intestinal tract under extreme conditions includes the following stages:

Step 1. Artificial gastric juice was prepared with the following composition: Pepsin (Sigma, P7000)—0.175% (w/v); NaCl—0.2% (w/v); pH 2.5 and to 9 ml of it is added 1 ml water solution of Sample IV1 (dilution 1:1). The sample provisionally designated GJ, was incubated at 37° C. in an anaerobic environment for 2 hours. The measurement of the number of lactic acid microorganisms (cfu/ml) in sample GJ was done at 0 hour; 0.5 hour; 1 hour and 2 hour.

Step 2. 1 ml of sample GJ, incubated for 2 hours, provisionally designated GJ-2, was added to 9 ml gastric juice with the following composition: NaCl—0.2% (w/v); NaHCO3—1.1% (w/v); Trypsin (Sigma, T7409)—0.20; 2% (w/v); bile salts (Oxoid, Code L55)—0.9% and pH 8.0. The newly obtained sample, provisionally designated IJ, was incubated at 37° C. in an anaerobic environment for 5 hours. The number of microorganisms in sample IJ was measured and reported at 0 hour; 2.5 hour and 5 hour. The detection threshold of lactic acid microorganisms in this analysis was $10^3$ cfu/ml.

The results of the probiotic association survival rate analysis, in digestive juice are summarized in Tables 5 and 6 below. Table 5 in particular shows the results related to the survival rate of separate groups of lactic acid bacteria in product IV1 in artificial gastric juice (sample GJ).

TABLE 5

| | Number of microorganisms in sample GJ (cfu/ml) | | | | |
|---|---|---|---|---|---|
| Incubation time of sample GJ | *Streptococcus thermophilus* | *Lactobacillus delbrueckii* ssp. *lactis* | *Lactobacillus delbrueckii* ssp. *bulgaricus* | *Lactobacillus helveticus* | Total number of lactic acid microorganisms |
| 0 hour | $5.9 \times 10^7$ | $7.8 \times 10^6$ | $2.9 \times 10^7$ | $2.8 \times 10^7$ | $1.2 \times 10^8$ |
| 0.5 hour | $4.8 \times 10^7$ | $6.1 \times 10^6$ | $2.4 \times 10^7$ | $2.5 \times 10^7$ | $1 \times 10^8$ |
| 1 hour | $3.7 \times 10^7$ | $5.7 \times 10^6$ | $1.8 \times 10^7$ | $2.1 \times 10^7$ | $8.2 \times 10^7$ |
| 2 hour | $1.3 \times 10^7$ | $2.5 \times 10^6$ | $9 \times 10^6$ | $1.1 \times 10^7$ | $3.6 \times 10^7$ |

As shown in Table 5, the lactic acid bacteria in the probiotic product IV1 survive in artificial gastric juice as follows: 83% survive for 30 minutes, 68% survive for an hour and 30% survive for 2 hours.

The results of the survival rate of separate groups of lactic acid bacteria in the product IV1 in artificial gastric juice (sample IJ) are presented in Table 6 below:

TABLE 6

| Incubation time of sample IJ | Number of microorganisms in sample IJ (cfu/ml) | | | | |
|---|---|---|---|---|---|
| | Streptococcus thermophilus | Lactobacillus delbrueckii ssp. lactis | Lactobacillus delbrueckii ssp. bulgaricus | Lactobacillus helveticus | Total number of lactic acid microorganisms |
| 0 hour | $1.3 \times 10^7$ | $2.5 \times 10^6$ | $9 \times 10^6$ | $1.1 \times 10^7$ | $3.6 \times 10^7$ |
| 2.5 hours | $1.9 \times 10^7$ | $1.8 \times 10^6$ | $5.2 \times 10^6$ | $4.5 \times 10^6$ | $3.1 \times 10^7$ |
| 5 hours | $8.7 \times 10^5$ | $6.6 \times 10^5$ | $9.2 \times 10^4$ | $8.6 \times 10^6$ | $1.1 \times 10^7$ |

The results summarized in Table 6 show that about 10% of the lactic acid bacteria (LAB) in the rehydrated probiotic product IV1 survive in the extreme conditions of both stages of the analysis—2 hours in artificial gastric juice followed by 5 hours in artificial intestinal juice. In the $7^{th}$ hour of the research, the sample IV1 contained live probiotic microorganisms and the quantitative value was over $10^7$. Of all the kinds of lactic acid bacteria contained in sample IV1, the kind that shows the best survival rate was *Lactobacillus helveticus*.

The results show also that the probiotic associations, according to the invention, demonstrate a very good survival rate and resistance after rehydration in the extreme conditions of human stomach and intestines. The microorganisms contained in the dietary products, as per the invention, put in extreme conditions remain within the quantitative value of above $1 \times 10^7$, which is enough to adhere to the intestines wall and reproduce.

Example 7

Proof of Antimicrobial Activity of Probiotic Association

The antimicrobial activity of the probiotic association was proven through ascertaining bacteriostatic and bacteriocide effects of a sample of dry product (sample IV1) through the well-diffusion method. The relations between the freeze-dried product and pathogenic microorganisms have been studied—reference cultures, clinically isolated (intestines/faeces) and isolated from food pathogens of the following types: *Escherichia coli* serotypes O6, O44 and O127, *Salmonella* groups C, B, D; *Shigella flexneri, Listeria monocytogenes, Proteus mirabilis, Enterobacter sakazakii* and *Staphylococcus aureus, Enterobacter aerogenes*.

In order to analyze bacteriostatic and bacteriocide effects, a culture of pathogenic microorganisms was cultivated on Nutrient agar (MERCK, 1.00427.0500), to which was added 0.5% of bile salts in a concentration of $10^5$ cfu/ml, and the product was rehydrated in advance with sterile distilled water in a ratio of 1:3. The wells in which the product was placed had the capacity of 50 µl. The inoculations were incubated for 24 hours in an anaerobic environment. The results in regards to pathogenic microorganisms in which bateriocide (BC) and/or bacteriostatic (BS) effect was demonstrated are registered as mm sterile zone or suppression zone and are summarized in Table 7 below. The results show that the product demonstrates good antimicrobial activity, which includes a remarkable bacteriostatic effect and moderate bacteriocide effect.

TABLE 7

| IV 1, pH 5.9 | | |
|---|---|---|
| Pathogen | BC (mm) | BS (mm) |
| *P. mirabilis* | 1 | 3 |
| *Shigella flexneri* | 0 | 3 |
| *S. aureus* 361 | 5 | 5 |
| *S. aureus* 746 | 2 | 4 |
| *Salmonella* gr. B | 0 | 2 |
| *E. coli* O-44 | 0 | 2 |

In addition, the research concerning product safety presented in Table 8 below, shows that the products containing probiotic lactic acid microorganisms association, according to the invention, are safe for people.

TABLE 8

| INDICATORS | ANALYSIS METHODS | CHARACTERISTICS AND NORMS | RESULTS |
|---|---|---|---|
| Heavy metals and other toxic elements, mg/kg, no more than: | Arsenic under BDS EN 14546:2006 Lead, cadmium, copper under BDS EN 14084:2003 Mercury under BDS EN 13806:2003 | Copper - 3.0; lead - 1.0; arsenic - 2.0; Cadmium - 0.1; mercury - 0.04; | Meets the requirements |

TABLE 8-continued

| INDICATORS | ANALYSIS METHODS | CHARACTERISTICS AND NORMS | RESULTS |
|---|---|---|---|
| Total number of mesophilic aerobic and facutative anaerobic non-lactic acid bacteria, CFU/g, not more than: | BDS ISO 6610 | 1000 (1.0 · 10$^3$) | Meets the requirements |
| Coliforms in 1.0 g of the product: | BDS ISO 4831 | To be established | Meets the requirements |
| Yeast and mold in 1.0 g of the product: | BDS ISO 6611 | To be established | Meets the requirements |
| Microscopic mold fungi spores B 1.0 g of the product: | BDS ISO 6611 | To be established | Meets the requirements |
| *Salmonella* species in 0.25 g of the product: | BDS ISO 6579 | To be established | Meets the requirements |
| Coagulasopositive *staphylococci* (*S. aureus*) in 1.0 g of the product: | BDS ISO 6888-1, 2, 3 | To be established | Meets the requirements |
| *Listeria monocytogenes* in 25.0 g of the product: | BDS ISO 11290-1 | To be established | Meets the requirements |
| Aflatoxin M1 mg/kg | BDS 16242-85 | No more than 0.5 | Meets the requirements |

Example 8

Food Supplements for Healthy Human Nutrition Added to Coffee

In order to obtain food supplements for healthy human nutrition added to coffee, 4 g of dietary milk product was obtained as described in Example 3. Then, 2 g of instant coffee or decaf coffee was added, in addition to 2 g of creamer and 2 g of dextrose monohydrate. The mixture was homogenized and wrapped in aluminium foil. The resulting product has a refreshing and healthy effect when consumed.

Example 9

Food Supplement for Healthy Human Nutrition Containing Blueberry Extract

In order to manufacture capsules of a dietary product containing blueberry extract, 240 mg of product obtained as described in Example 5 was added to 10 mg of dry blueberry extract, standardized to 25% contents of Anthocyanins and 20 mg dextrose monohydrate. The obtained mixture was homogenized and placed in a plant capsule. The product was used as a food supplement for maintaining the overall health and eyesight, in particular.

Example 10

Food Supplements Containing Papaya Extract

In order to obtain capsules of a dietary product containing papaya extract, 250 mg of product obtained as described in Example 5 were added to 15 mg of dry papaya extract and 20 mg of dextrose monohydrate. The obtained mixture was homogenized and placed in a gelatin capsule. The product was used for maintaining and optimising the body weight.

The invention illustratively disclosed herein suitably may be practiced in the absence of any element, which is not specifically disclosed herein. It is apparent to those skilled in the art, however, that many changes, variations, modifications, other uses, and applications to the method are possible, and also changes, variations, modifications, other uses, and applications which do not depart from the spirit and scope of the invention are deemed to be covered by the invention, which is limited only by the claims which follow.

What is claimed is:

1. A method of producing a dietary product comprising:
   a) mixing spring water from Mountain Stara Planina in Northern Bulgaria with pasteurized milk in a ratio of about 1:2 (v/v) to allow microorganisms in the spring water to multiply and to produce a starter material wherein the microorganisms in the spring water comprise strains: *Lactobacillus delbruecki* subsp. *bulgaricus* DWT1 registered in CCM under no. 7992, *Lactobacillus helveticus* DWT2 registered in CCM under no. 7993, *Lactobacillus delbrueckii* subsp. *lactis* DWT3 registered in CCM under no. 7994, *Streptococcus thermophilus* DWT4 registered in CCM under no. 7992, *Streptococcus thermophilus* DWT5 registered in CCM under no. 7993, *Streptococcus thermophilus* DWT6 registered in CCM under no. 7994, *Streptococcus thermophilus* DWT7 registered in CCM under no. 7995 and *Streptococcus thermophilus* DWT8 registered in CCM under no. 7996;
   b) mixing the starter material of step a) with pasteurized milk in a ratio of about 3:10 (g/L) to allow fermentation; and,
   c) lyophilizing the fermentation product to produce a dietary product.

2. The method of claim 1 further comprising combining the dietary product with a nutritional supplement.

3. The method of claim 1, wherein the dietary product is shelf stable for at least 12 months.

4. The method of claim 1, wherein the dietary product is shelf stable for at least 22 months.

5. A method of producing a starter material, the method comprising mixing spring water from Mountain Stara Planina in Northern Bulgaria with pasteurized milk in a ratio of about 1:2 (v/v) to allow microorganisms in the spring water to multiply and to produce a biomass for use as a starter material starter material; wherein the microorganisms in the spring water comprise strains: *Lactobacillus delbrueckii* subsp. *bulgaricus* DWT1 registered in CCM under no. 7992, *Lactobacillus helveticus* DWT2 registered in CCM under no. 7993, *Lactobacillus delbrueckii* subsp. *lactis* DWT3 registered in CCM under no. 7994, *Streptococcus thermophilus* DWT4 registered in CCM under no. 7992, *Streptococcus thermophilus* DWT5 registered in CCM under no. 7993, *Streptococcus thermophilus* DWT6 registered in CCM under no. 7994, *Streptococcus thermophilus* DWT7 registered in CCM under no. 7995 and *Streptococcus thermophilus* DWT8 registered in CCM under no. 7996.

6. A method of producing a dietary product comprising:
   a) mixing a starter material obtained from using the method of claim 5 with pasteurized milk in a ratio of about 3:10 (g/L) to allow fermentation; and
   b) lyophilizing the fermentation product of step a) to produce a dietary product.

7. The method of claim 6, wherein the dietary product after lyophilizing contains alive cells of probiotic association with concentration from $8.0 \times 10^7$ cfu/g to $1.2 \times 10^8$ cfu/g,
   wherein the concentration of alive cells of the strains *Streptococcus thermophilus* ranges from $4.6 \times 10^7$ cfu/g to $5.9 \times 10^7$ cfu/g, including the strain *Streptococcus thermophilus* DWT4, CCM reg. No. 7992, strain *Streptococcus thermophilus* DWT5, CCM reg. No. 7993, strain *Streptococcus thermophilus* DWT6, CCM reg. No. 7994, strain *Streptococcus thermophilus* DWT7, CCM reg. No. 7995 and strain *Streptococcus thermophilus* DWT8, CCM reg. No. 7996;
   wherein the concentration of alive cells of strain *Lactobacillus delbrueckii* subsp. *lactis*, CCM reg. No. 7994 ranges from $6.1 \times 10^6$ cfu/g to $7.8 \times 10^6$ cfu/g,
   wherein the concentration of alive cells of strain *Lactobacillus delbruecki* subsp. *bulgaricus*, CCM reg. No. 7992 ranges from $1.4 \times 10^7$ cfu/g to $2.9 \times 10^7$ cfu/g and the concentration of alive cells of the strain *Lactobacillus helveticus*, CCM reg. No. 7993 ranges from $1.4 \times 10^7$ to $2.8 \times 10^7$ cfu/g.

8. The method of claim 6, wherein the dietary product after rehydration and in the extreme conditions of the gastro-intestinal tract contains a concentration no less than $1.1 \times 10^7$ cfu/g of alive cells of the strain selected from *Lactobacillus delbrueckii* subsp. *bulgaricus* DWT1 registered in CCM under no. 7992, *Lactobacillus helveticus* DWT2 registered in CCM under no. 7993, *Lactobacillus delbrueckii* subsp. *lactis* DWT3 registered in CCM under no. 7994, *Streptococcus thermophilus* DWT4 registered in CCM under no. 7992, *Streptococcus thermophilus* DWT5 registered in CCM under no. 7993, *Streptococcus thermophilus* DWT6 registered in CCM under no. 7994, *Streptococcus thermophilus* DWT7 registered in CCM under no. 7995, and *Streptococcus thermophilus* DWT8 registered in CCM under no. 7996.

9. A method of producing a dry starter culture comprising:
   a) mixing about 3 gram of a starter material obtained from using the method of claim 5 to every 10 litres of pasteurized milk to allow fermentation and produce a liquid culture;
   b) mixing the liquid culture from step a) with pasteurized milk in a ratio of about 1:60 (v/v) to make a mixture and to allow fermentation;
   c) neutralizing the mixture of step b), if necessary, to optimize pH for the fermentation; and
   d) lyophilizing the fermentation product of step b) or c) to produce the dry starter culture.

10. A method of producing a dietary product comprising:
    a) mixing a dry starter culture obtained from using the method of claim 9 with pasteurized milk in a ratio of about 3:5 (g/L) to allow fermentation; and
    b) lyophilizing the fermentation product of step a) to produce a dietary product.

11. The method of claim 2, wherein the nutritional supplement in the dietary product is selected from the group consisting of coffee, cocoa, blueberry extract, papaya extract, oils, honey, dry plant extracts, fibers, enzymes, and any combinations thereof.

* * * * *